(12) United States Patent
Jönsson

(10) Patent No.: US 10,688,288 B2
(45) Date of Patent: Jun. 23, 2020

(54) CATHETER DEVICE AND METHOD FOR DELIVERY OF MEDICAL DEVICES IN THE AORTA

(71) Applicant: ITSO Medical AB, Helsingborg (SE)

(72) Inventor: Anders Jönsson, Bromma (SE)

(73) Assignee: ITSO Medical AB, Helsingborg (SE)

( * ) Notice: Subject to any disclaimer, the term of this patent is extended or adjusted under 35 U.S.C. 154(b) by 0 days.

(21) Appl. No.: 16/467,008

(22) PCT Filed: Dec. 5, 2017

(86) PCT No.: PCT/SE2017/051221
§ 371 (c)(1),
(2) Date: Jun. 5, 2019

(87) PCT Pub. No.: WO2018/106171
PCT Pub. Date: Jun. 14, 2018

(65) Prior Publication Data
US 2019/0388657 A1 Dec. 26, 2019

(30) Foreign Application Priority Data
Dec. 5, 2016 (SE) ..................... 1651598

(51) Int. Cl.
A61M 25/10 (2013.01)
A61F 2/24 (2006.01)
A61F 2/01 (2006.01)

(52) U.S. Cl.
CPC ......... A61M 25/1002 (2013.01); A61F 2/013 (2013.01); A61F 2/2436 (2013.01); A61F 2002/011 (2013.01); A61M 2025/1047 (2013.01); A61M 2025/1095 (2013.01)

(58) Field of Classification Search
CPC ....... A61M 25/1002; A61M 2025/1047; A61F 2/2436; A61F 2/013; A61F 2002/011
See application file for complete search history.

(56) References Cited

U.S. PATENT DOCUMENTS

| 5,827,237 A | 10/1998 | Macoviak et al. |
| 2009/0030510 A1 | 1/2009 | Ho |
| 2012/0209375 A1 | 8/2012 | Madrid et al. |
| 2014/0180329 A1 | 6/2014 | Krahbichler |

FOREIGN PATENT DOCUMENTS

WO  WO2015/177322 A1  11/2015

OTHER PUBLICATIONS

WIPO, International Preliminary Examining Authority (Swedish Patent and Trademark Office), International Preliminary Report on Patentability dated Mar. 28, 2019 in International Patent Application No. PCT/SE2017/051221, 14 pages.
WIPO, Swedish International Search Authority, International Search Report and Written Opinion dated Feb. 14, 2018 in International Patent Application No. PCT/SE2017/051221, 14 pages.

Primary Examiner — Julie A Szpira
(74) Attorney, Agent, or Firm — Inskeep IP Group, Inc.

(57) ABSTRACT

A catheter device and method are disclosed for transvascular delivery of a medical device to a cardiac valve region of a patient. The catheter device comprises an elongate sheath with a lumen and a distal end for positioning at a target site e.g. a heart valve.

17 Claims, 27 Drawing Sheets

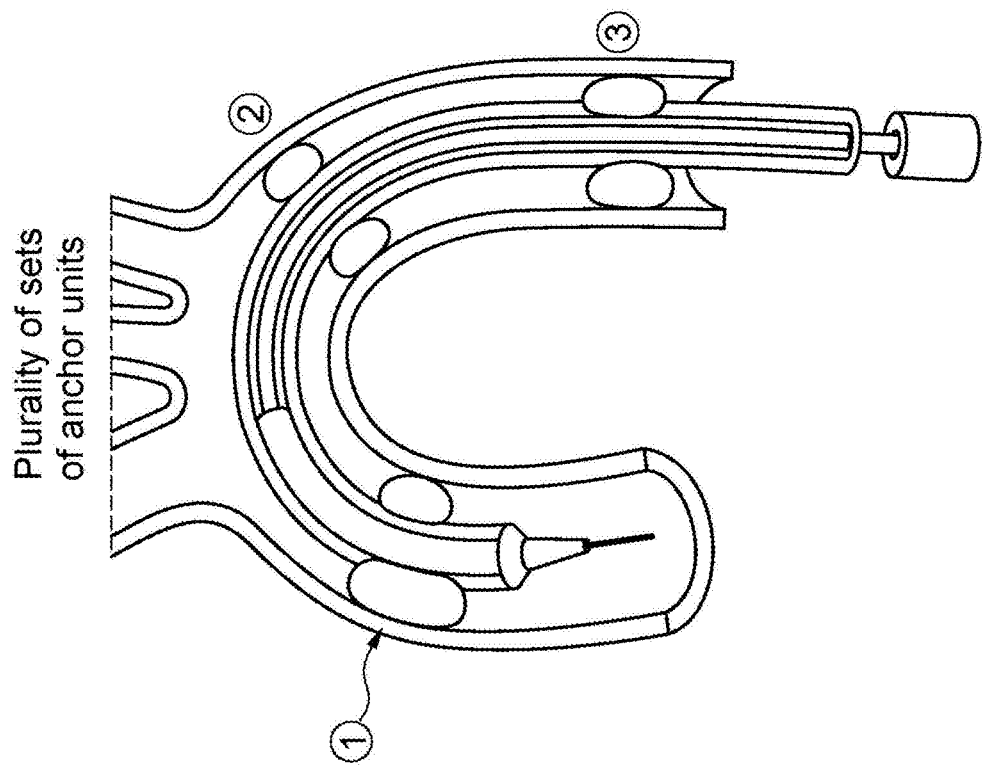
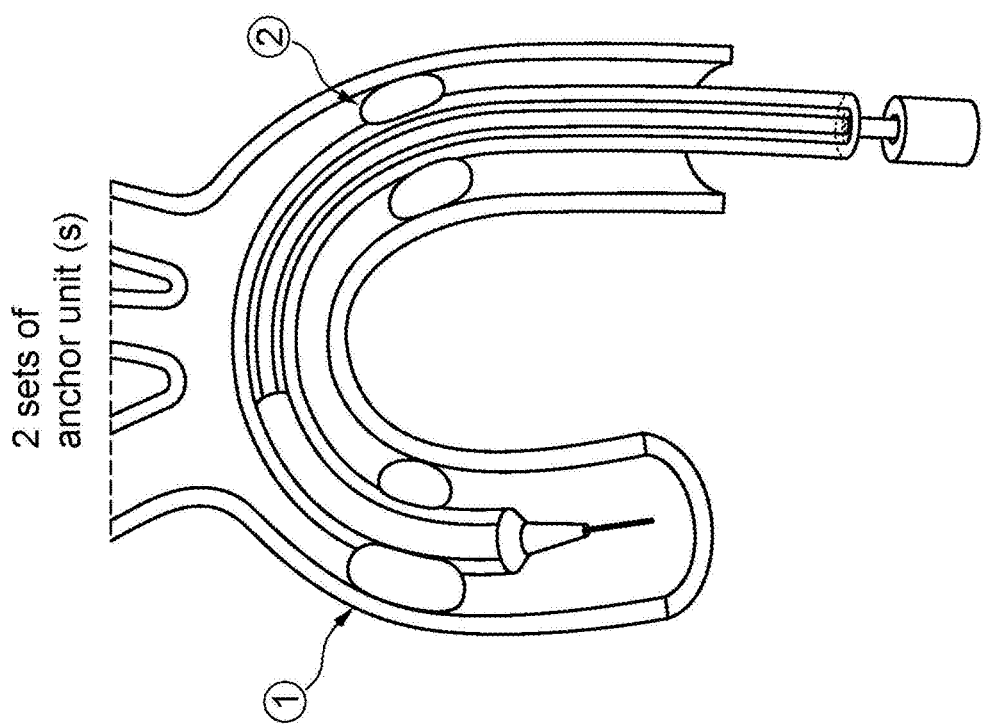
Fig. 9

Advantages
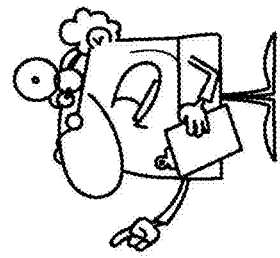
For patients
Better outcome
Less complications
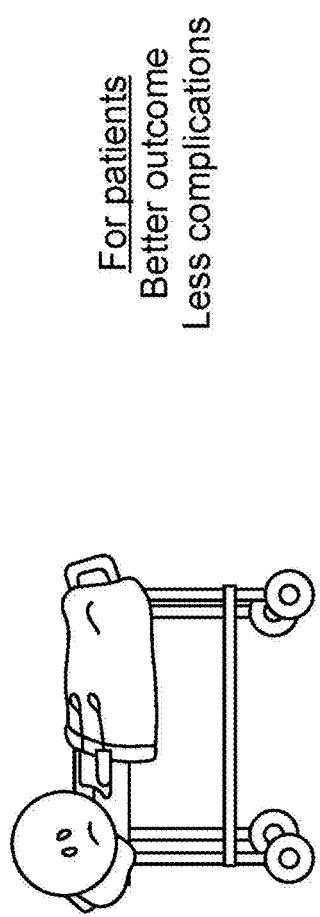
For clinicians
"Turns a large anatomy into a smaller"
Less complications
No disruption in clinical workflow
For healthcare provider
Avoids costly complications
Improve reputation
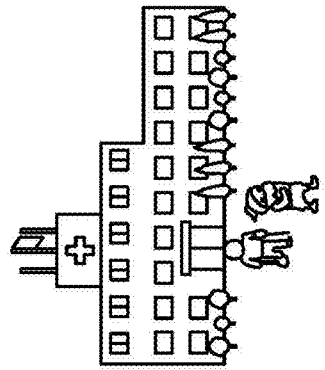
Fig. 10

Animal evaluation

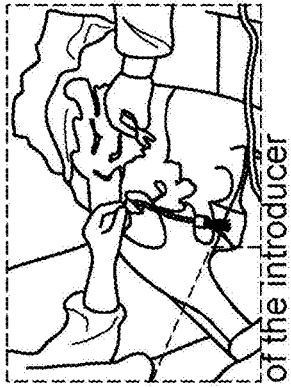
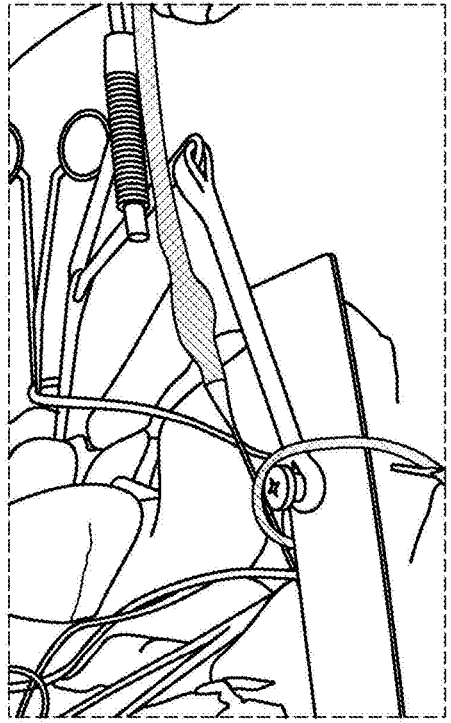
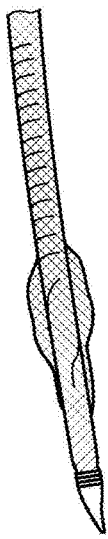

In the upper left panel the distal part of the introducer is seen with the two distal ballons un-inflated. The CoreValve delivery catheter is placed in the lumen of the introducer with its distal tip just outside the tip of the introducer.

In the lower left panel the same configuration is seen but now with the ballons filled with saline.

In the bottom panel the setup with introducer/CoreValve delivery catheter is pushed into the aorta over the guide wire in a pig.

Fig. 13

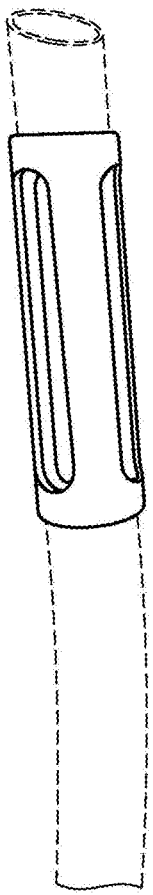

"crown" positioned exterior to single lobe balloon to create multiple lobe balloons (anchoring units)
Rigid webs that resist inflation pressure to create lobes expandable from interspaces between crowns webs Particularly well working with latex / rubber / elastic balloon(s) to create inflatable lobes Inflatable lobes adaptable to be in apposition with inner lumen wall of tubular body structures

Fig. 19

Perspective view of schematic illustration of crown

CATHETER DEVICE AND METHOD FOR DELIVERY OF MEDICAL DEVICES IN THE AORTA

RELATED APPLICATIONS

This application is the U.S. National Phase of and claims priority to International Patent Application No. PCT/SE2017/051221, International Filing Date Dec. 5, 2017, entitled Catheter Device And Method For Delivery Of Medical Devices In The Aorta; which claims benefit of Swedish Application No. 1651598-3 filed Dec. 5, 2016; both of which are incorporated herein by reference in their entireties.

FIELD OF THE INVENTION

This invention pertains in general to the field of medical devices and medical procedures applying such medical devices. More particularly, the invention relates to a catheter device for inserting medical devices into a lumen of a patient. such as the aortic arch, as well as related medical procedures and methods. In particular the invention relates to the positioning of catheters for the delivery of medical devices and the procedures, and more specifically to the transvascular delivery of a medical device to a cardiac valve.

BACKGROUND OF THE INVENTION

The human heart is a hollow muscular organ, responsible for pumping a large volume of blood around the human body every day. The ability to pump the blood is facilitated by several heart valves which open and close appropriately to allow blood passage through the heart. Heart valve dysfunction through natural defects or through the increasing incidence of heart disease, often requires the dysfunctional valve to be treated, with the main treatment modalities being mechanical adjustment of the valve or replacing the valve altogether. Current medical techniques are aimed at moving away from the major open heart surgery procedure, which is very traumatic for the patient, to more minimally invasive catheter based procedures, which are less traumatic, although more complicated procedures.

Catheter based procedures require precise positioning of the catheter, used to deliver for example the replacement valve, in an optimal position in relation to the cardiac valve to be treated. This is especially important as misalignment has the potential to damage adjacent cardiac structures leading to severe coronary complications. Placement of the catheter adjacent to a heart valve is hampered by the fact that the heart continues to pump throughout the procedure, giving rise to significant levels of turbulence which the catheter has to overcome to maintain its position.

Hence, improved or alternative medical devices and procedures for stabilizing the introducer sheath during cardiac valve replacement would be advantageous, in particular allowing for increased cost-effectiveness, and/or patient safety.

SUMMARY OF THE INVENTION

Accordingly, embodiments of the present disclosure preferably seek to mitigate, alleviate or eliminate one or more deficiencies, disadvantages or issues in the art, such as the above-identified, singly or in any combination by providing a medical device and a method according to the appended patent claims.

The present disclosure is an introducer sheath that overcomes the positional problems that current catheters face. In addition to maintaining the position, the disclosure is so devised so that interference with the blood flow is minimal.

Aspects of the disclosure are described in the appended patent claims.

According to a first aspect, a catheter device is provided for transvascular delivery of a medical device to a target region of a patient is disclosed.

In another aspect, a method of transvascularly delivering a medical device to a target region of a patient is provided. The method comprises providing and minimally invasively introducing a catheter comprising an elongate sheath with a lumen to said target site.

Further embodiments of the disclosure are defined in the dependent claims, wherein features for the second and subsequent aspects of the disclosure are as for the first aspect mutatis mutandis.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the disclosure are capable of will be apparent and elucidated from the following description of embodiments of the present disclosure, reference being made to the accompanying drawings, in which.

Further figures are enclosed herein, wherein

Figure 6:
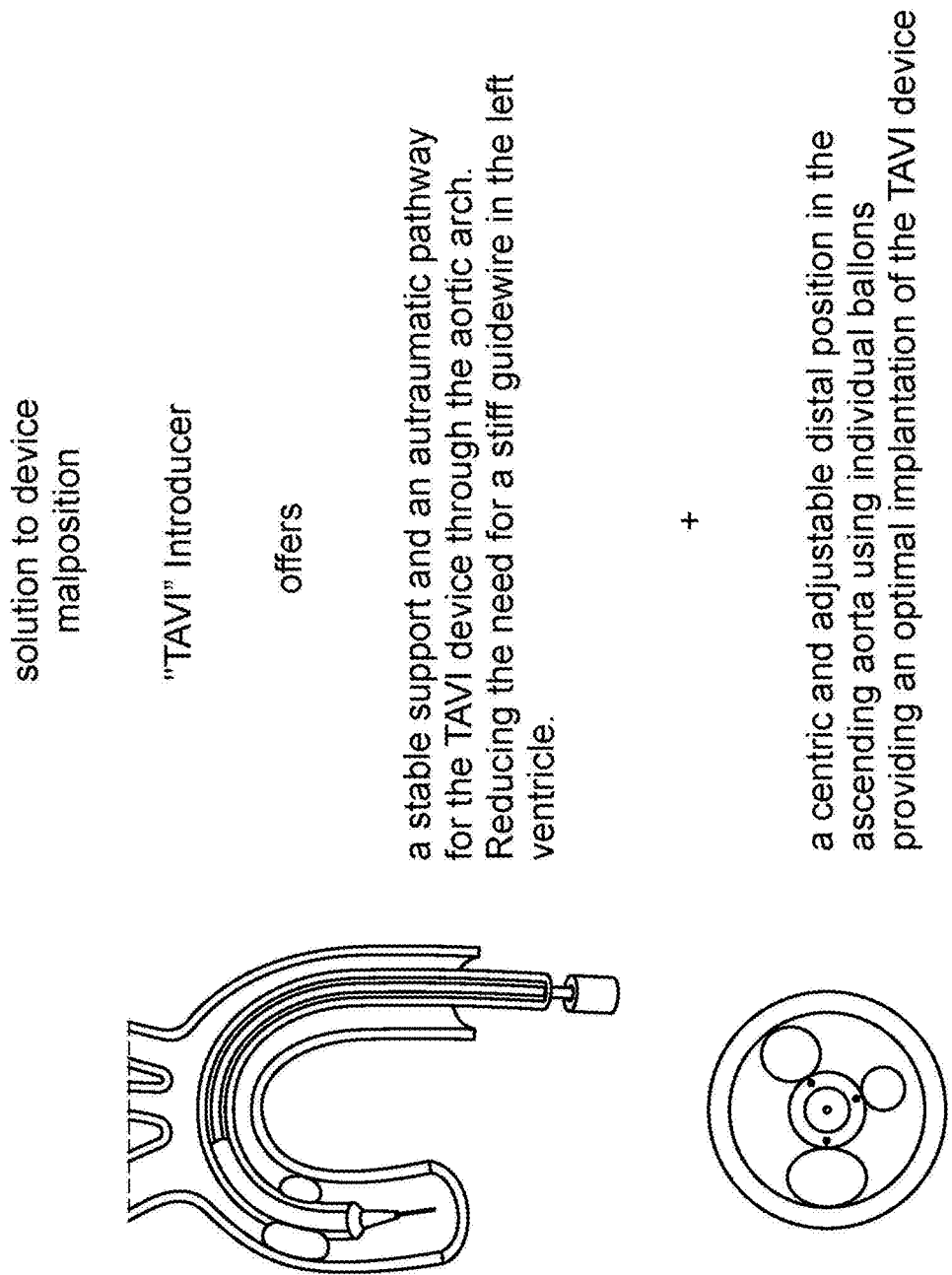
Figure 7:
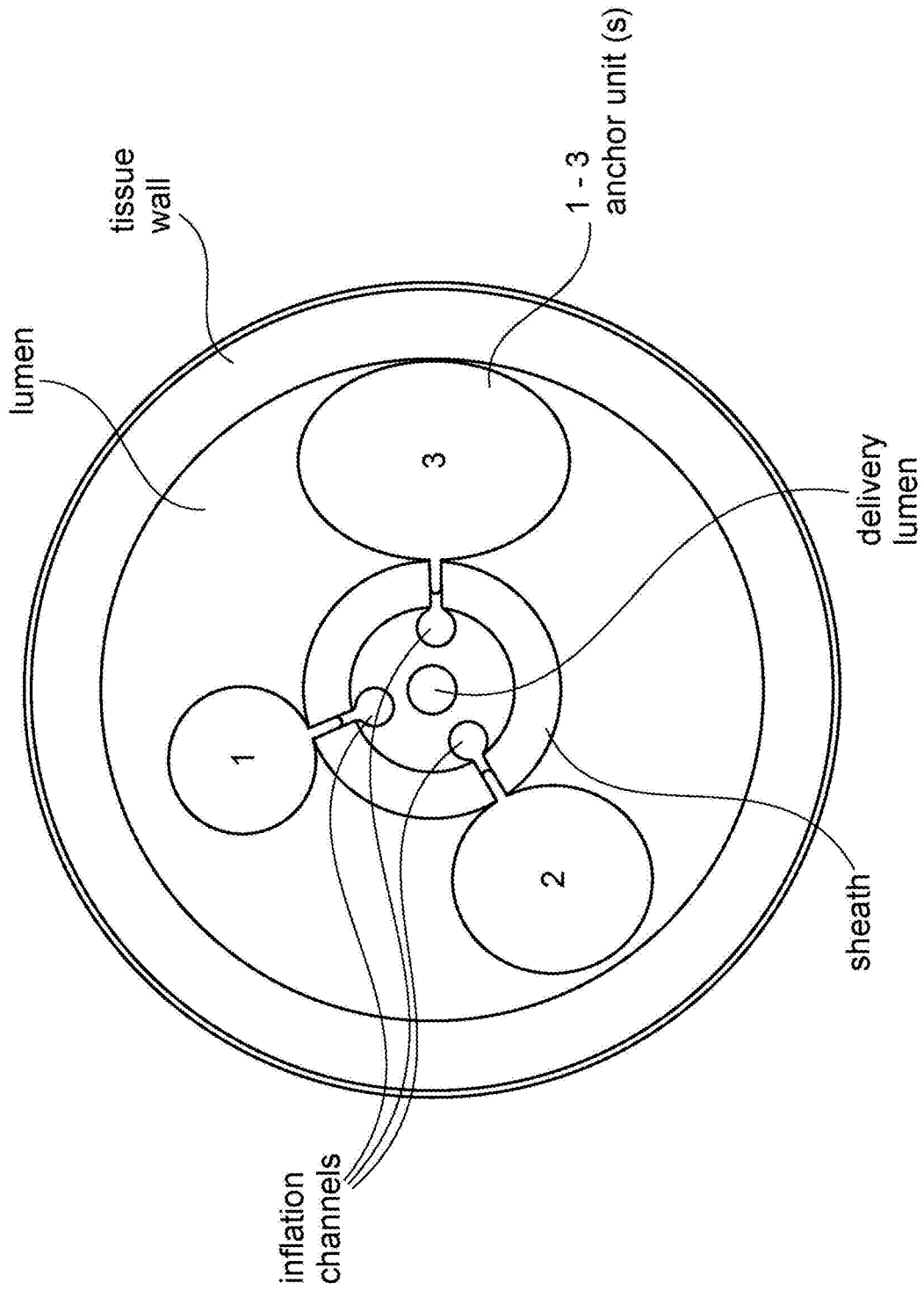
Figure 8:
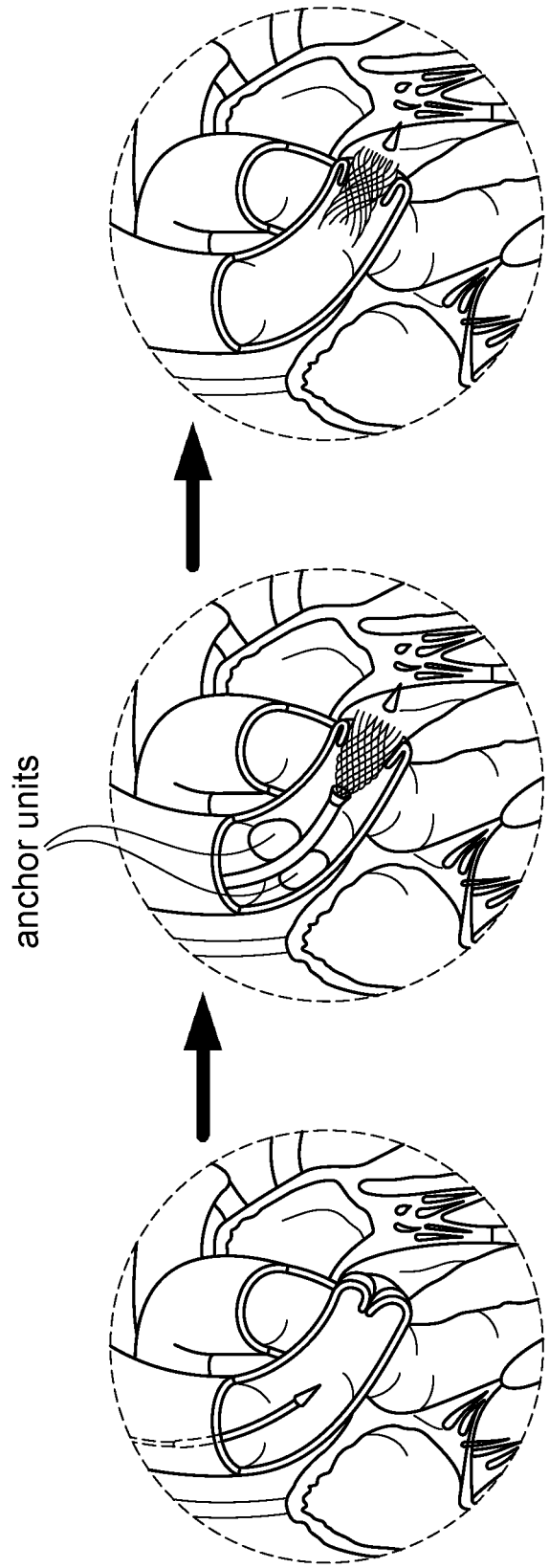
Figure 11:
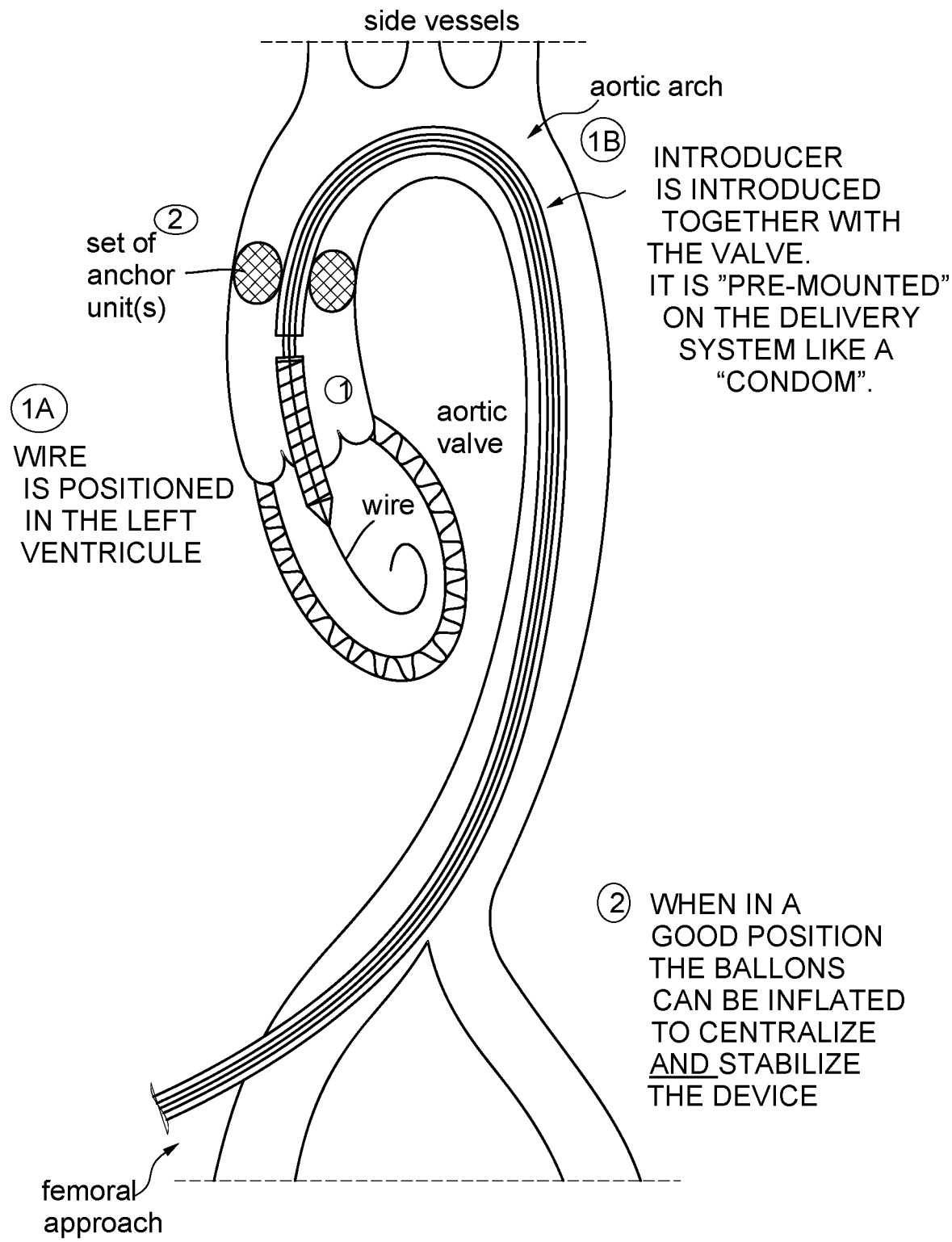
Figure 12:
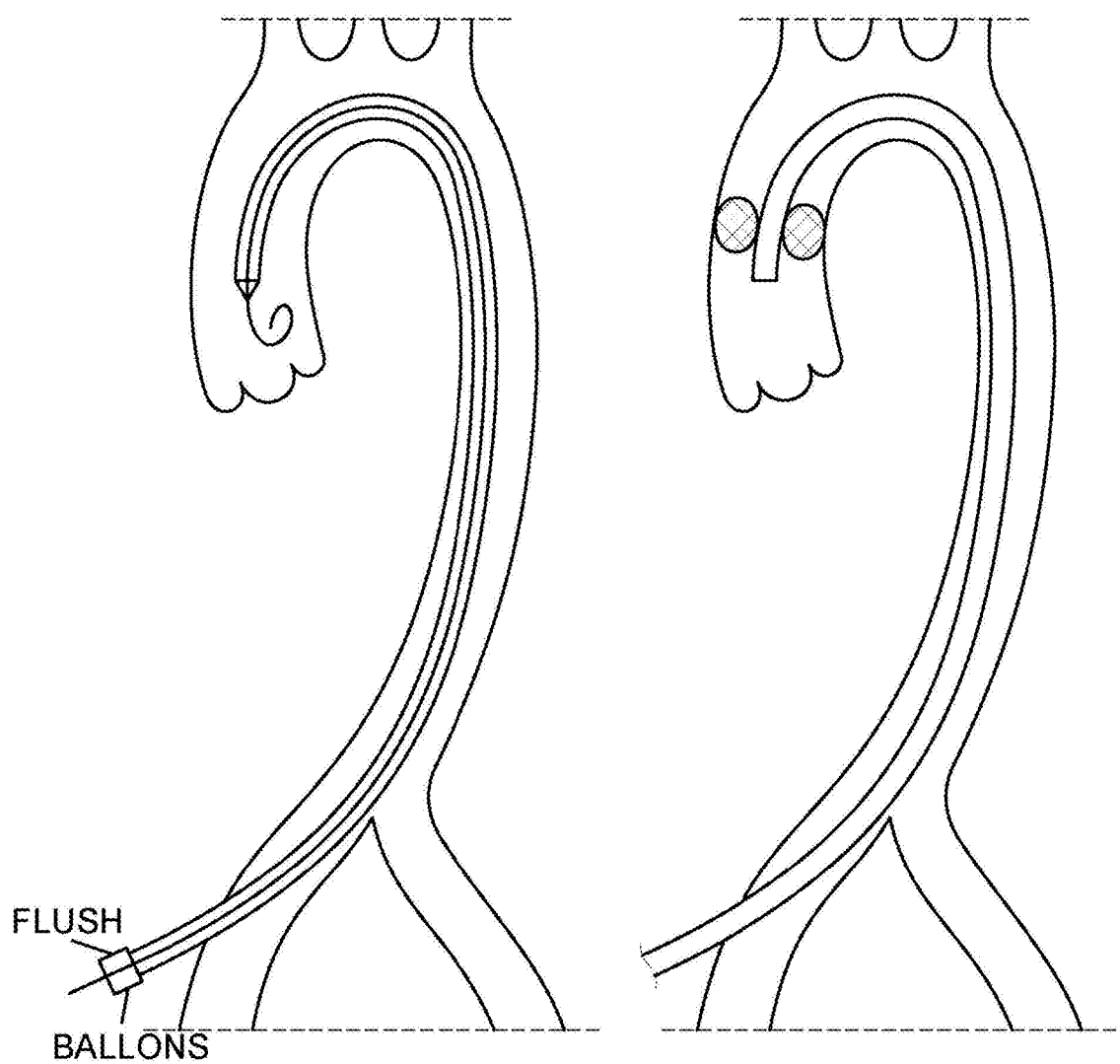
Figure 14:
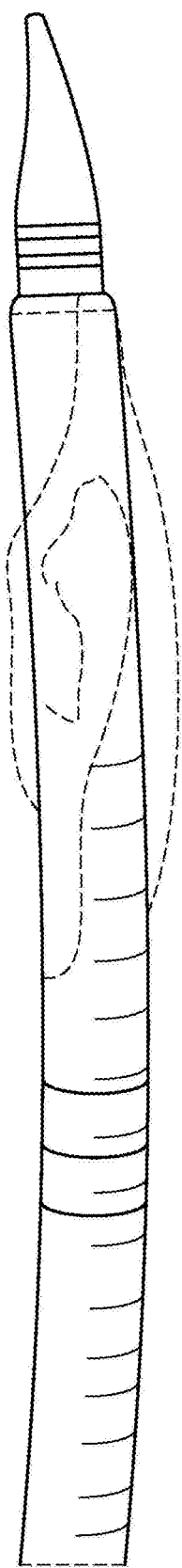
Figure 15:
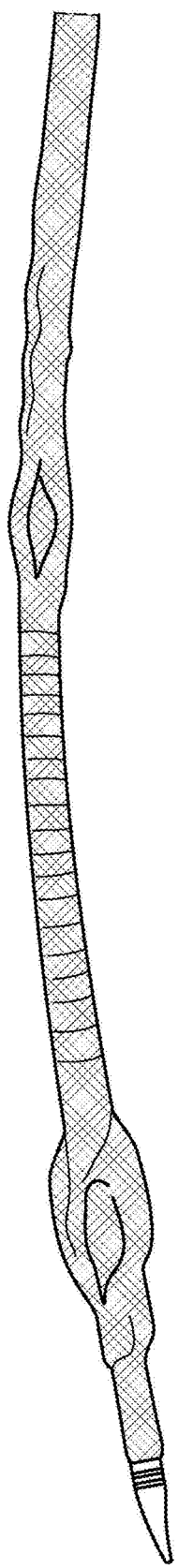
Figure 16:
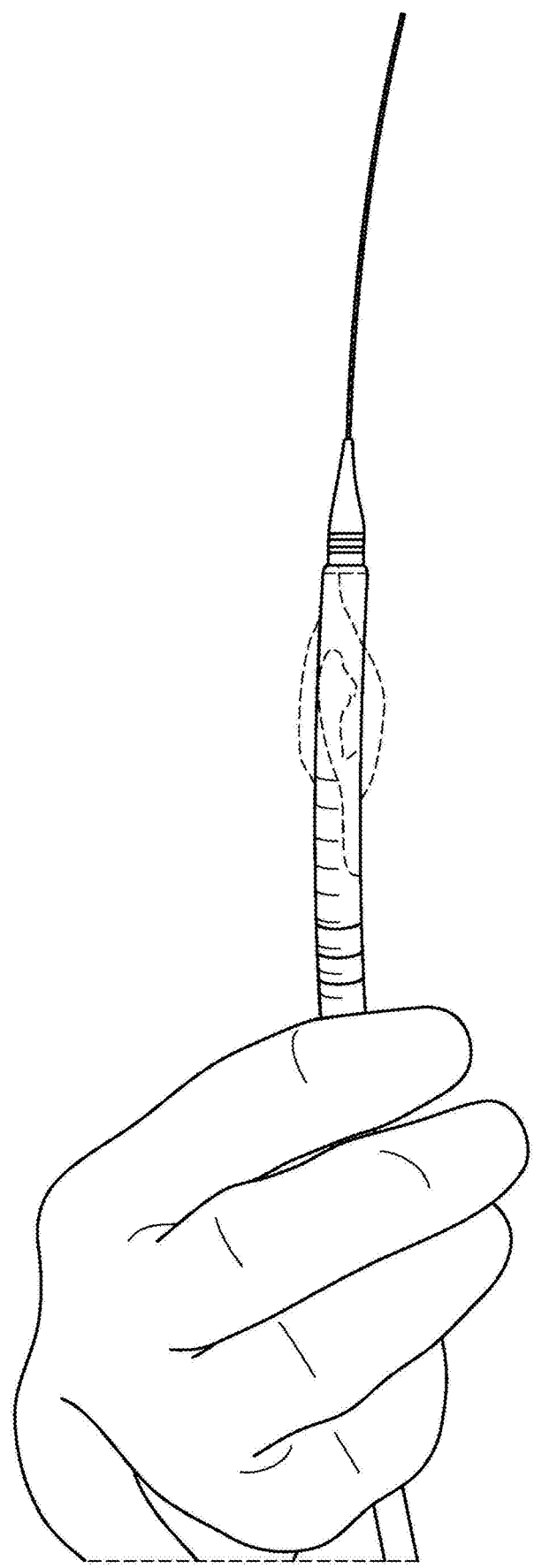
Figure 17:
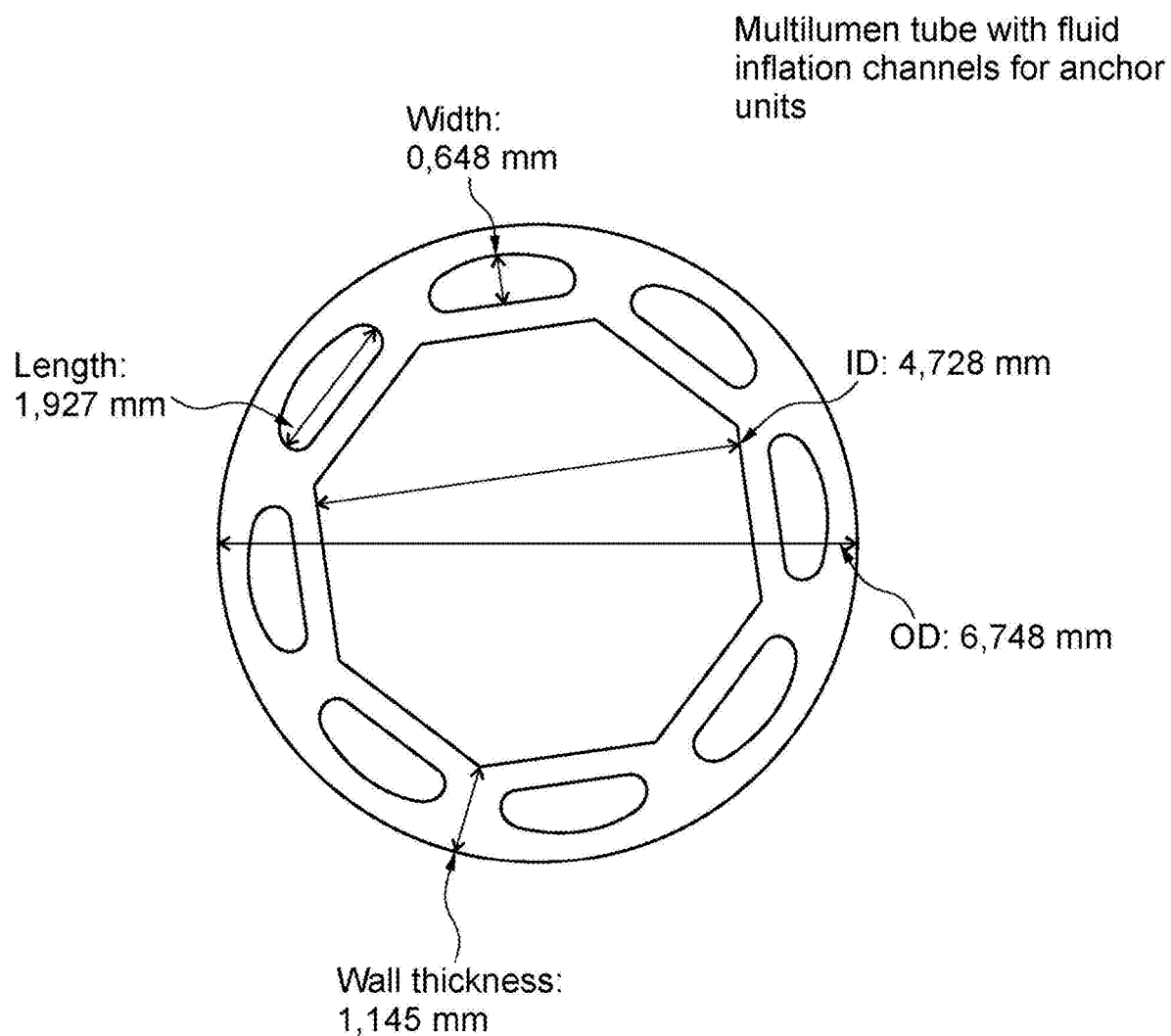
Figure 18:
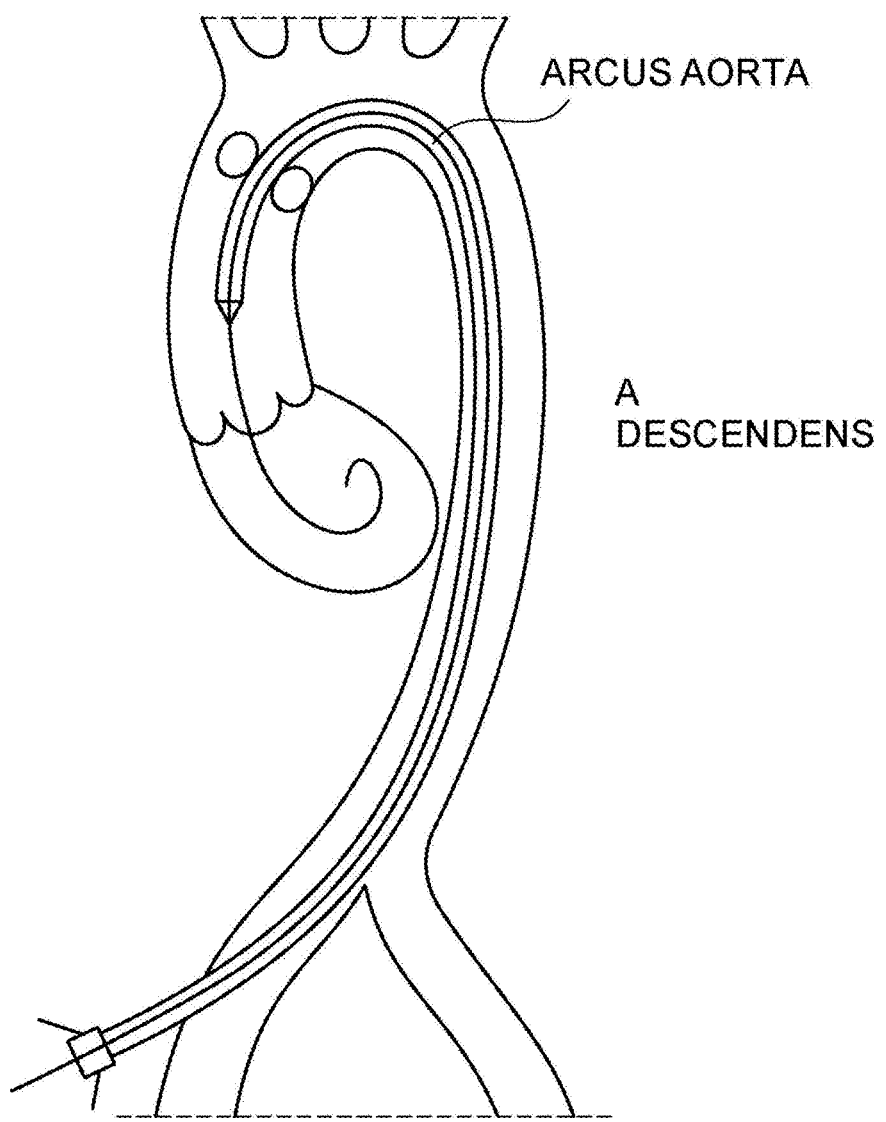
Figure 20:
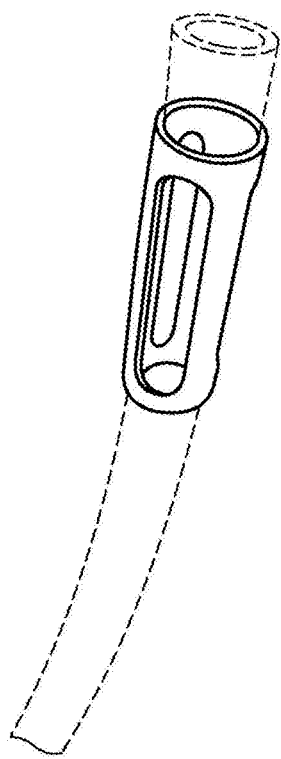

FIG. 6 is is a schematic illustration of a "TAVI" introducer installed in the aortic arch in two cross sectional views;

FIG. 7 is a cross-sectional view of a sheath with anchor units in a lumen;

FIG. 8 is an illustration of a TAVI procedure with a transfemoral approach using a Corevalve as an example;

FIG. 9 are two cross-sectional views similar to Fig. 6 showing two different embodiments of introducers having multiple sets of anchr units;

FIG. 10 is a schematic illustration of advantages for patients; clinicians and healthcare providers;

FIG. 11 is a cross-sectional view of an introducer inserted in a femoral approach to the aortic valve having a sheath according to the invention;

FIG. 12 are two cross sectional views of an introducer inserted over wire with a dilator to the aortic arch and the dilator removed and balloons inflated; respectively;

FIG. 13 are schematic illustrations of a distal part of an introducer with un-inflated balloons and inflated balloons; respectively; as well as a schematic illustration of an introducer/CoreValve pushed into the aorta of a pig;

FIG. 14 is a schematic illustration of an introducer with un-inflated balloons and a protruding dilator tip;

FIG. 15 is a schematic illustration of an introducer with a cover-sheath and inflated balloons and a protruding dilator tip;

FIG. 16 is a schematic illustration of user holding an introducer with a cover-sheath and balloons and a protruding dilator tip as well as a guidewire inserted into the dilator and distally protruding from the dilator;

FIG. 17 is cross section through an example of multi-lumen tube with fluid inflation channels for anchor units;

FIG. 18 is a cross-sectional view of an introducer inserted in a femoral approach to the aortic arch with anchor units; a dilator and guidewire;

FIG. 19 is a schematic illustration of a "crown" positioned over a single lobe balloon to create lobes expandable from interspaces of the crown when the balloon is inflated; and FIG. 20 is schematic illustration of a crown in a perspective view.

DESCRIPTION OF EMBODIMENTS

Specific embodiments of the disclosure will now be described with reference to the accompanying drawings. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art. The terminology used in the detailed description of the embodiments illustrated in the accompanying drawings is not intended to be limiting of the disclosure. In the drawings, like numbers refer to like elements.

Figure 1A:
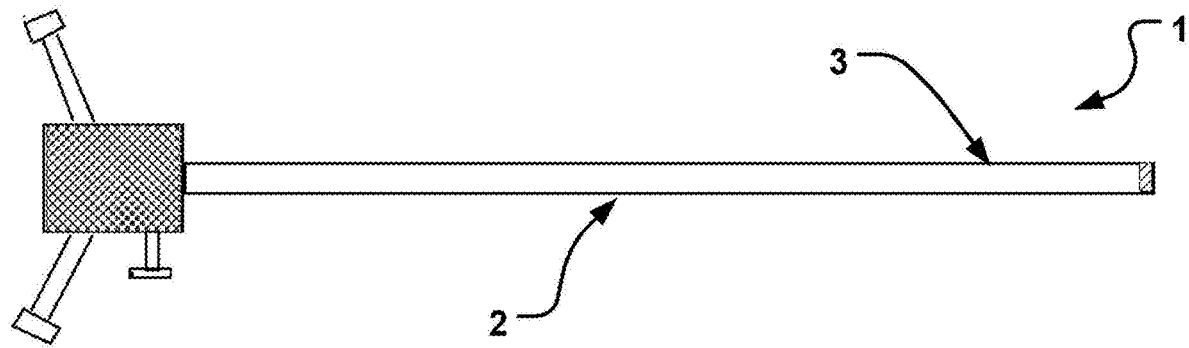
FIG. 1A is a schematic illustration of an elongate sheath connected to a hemostatic valve.
Figure 1B:
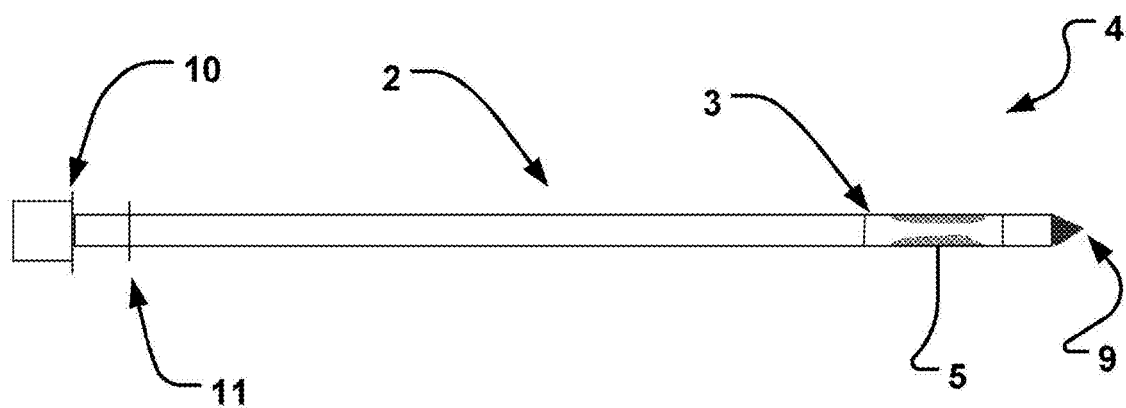
FIG. 1B is a schematic illustration of an elongate member, with the radially expandable units in the collapsed configuration.

In an embodiment of the disclosure according to FIG. 1A, a catheter device 1 for transvascular delivery of a medical device to a cardiac valve region 6 (see e.g. FIG. 4D) of a patient is shown. The catheter device comprises an elongate sheath 2 with a lumen and a distal end 3. In addition in FIG. 1B an elongate member 4 is provided with a distal end portion 9 comprising a plurality of radially expandable units 5. The end portion 9 may include an obturator. The expandable units 5 are arranged for temporarily positioning the elongate sheath 2 in relation to the cardiac valve 6, FIGS. 4B and 4F. The elongate member 4 is retractably insertable into the lumen of the elongate sheath 2.

The elongate sheath 2 depicted in FIG. 1A is designed to be deliverable transvascularly in the relaxed state which facilitates optimal flexibility when transiting through the vasculature. When at the desired anatomical location the elongate sheath 2 is able to be secured in position by means of the anchoring unit(s) stabilizing the sheath at the target location. The expandable anchoring units 5, facilitate optimal stabilization of the catheter 1 for subsequently affixing the medical device to the heart valve 6.

Figure 4A:
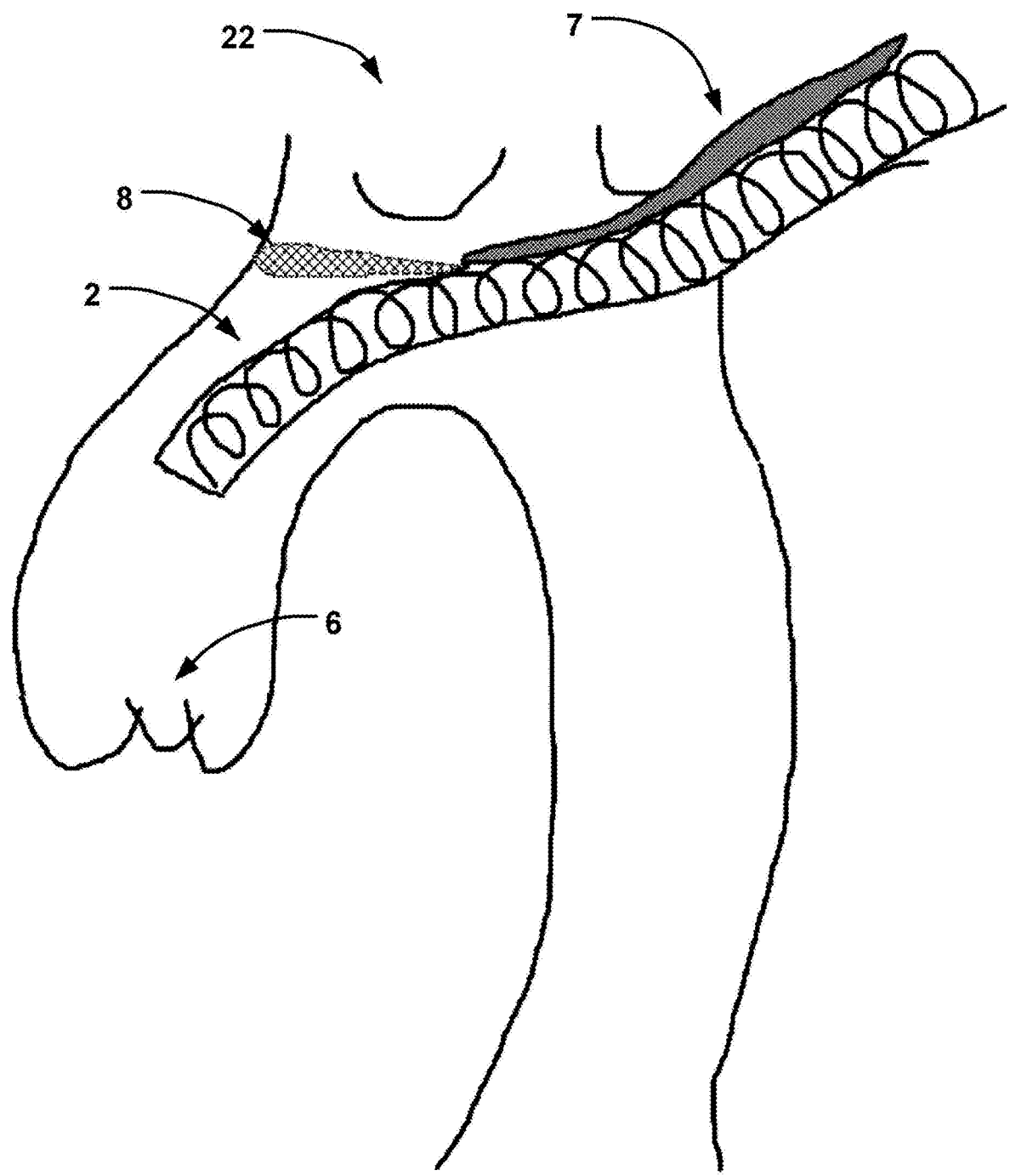
FIG. 4A is a schematic illustration of the elongate sheath delivered transaxillary to a cardiac valve, where an embolic protection filter is deployed, and the sheath is in a relaxed state.
Figure 4B:
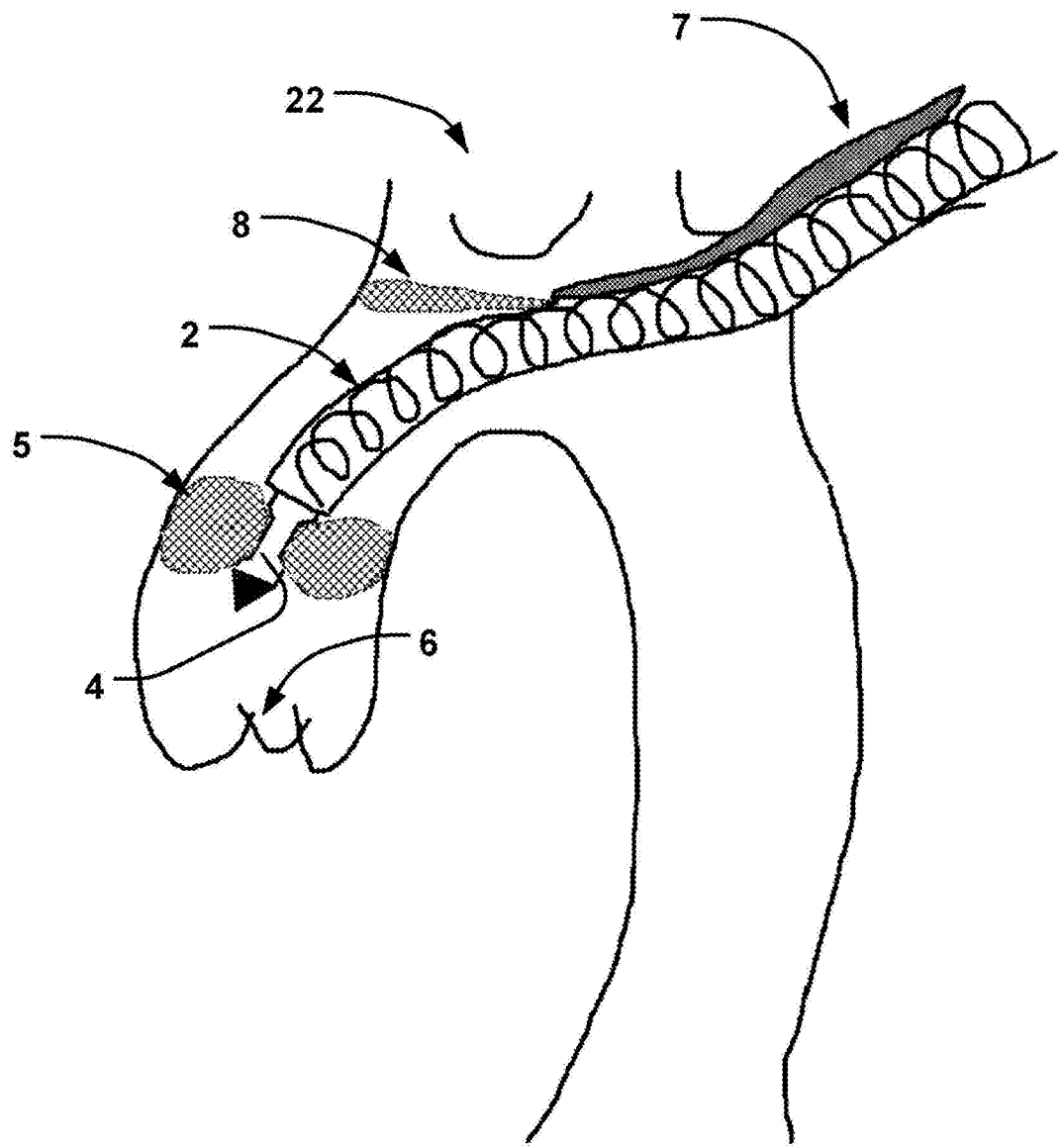
FIG. 4B is a schematic illustration where the relaxed sheath is positioned in relation to the cardiac valve by expandable units of an elongate member extending outside the distal end of the sheath.
Figure 4C:
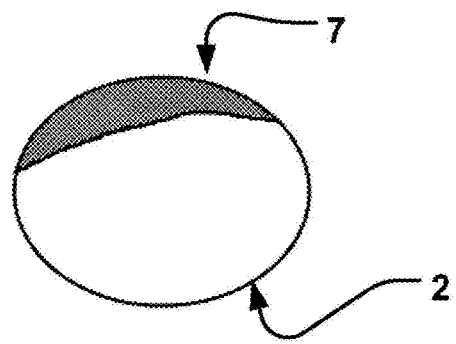
FIG. 4C is a schematic illustration of the cross sectional view of the elongate sheath incorporating a second channel for delivering the embolic protection filter.

FIG. 4A shows the elongate sheath inserted in its relaxed shape. FIG. 4B shows the radially expandable units 5 in their expanded configuration, i.e. outside the elongate sheath 2, which positions the elongate sheath 2 centrally over the valve 6. The expandable units 5 expand out of the elongate member 4, which extends beyond the distal end of the sheath 2.

The sheath 2 is now positioned and stabilized over the valve 6. This overcomes the problems in prior art with insufficient stabilization and lack of accurate positioning.

Alternatively, or in addition, expandable units, such as balloons may be arranged on the outside of the sheath 2. The sheath may be provided as a separate "condom" like sheath to be arranged outside an interior delivery catheter.

Arrangement may be made coaxially.

Figure 4D:
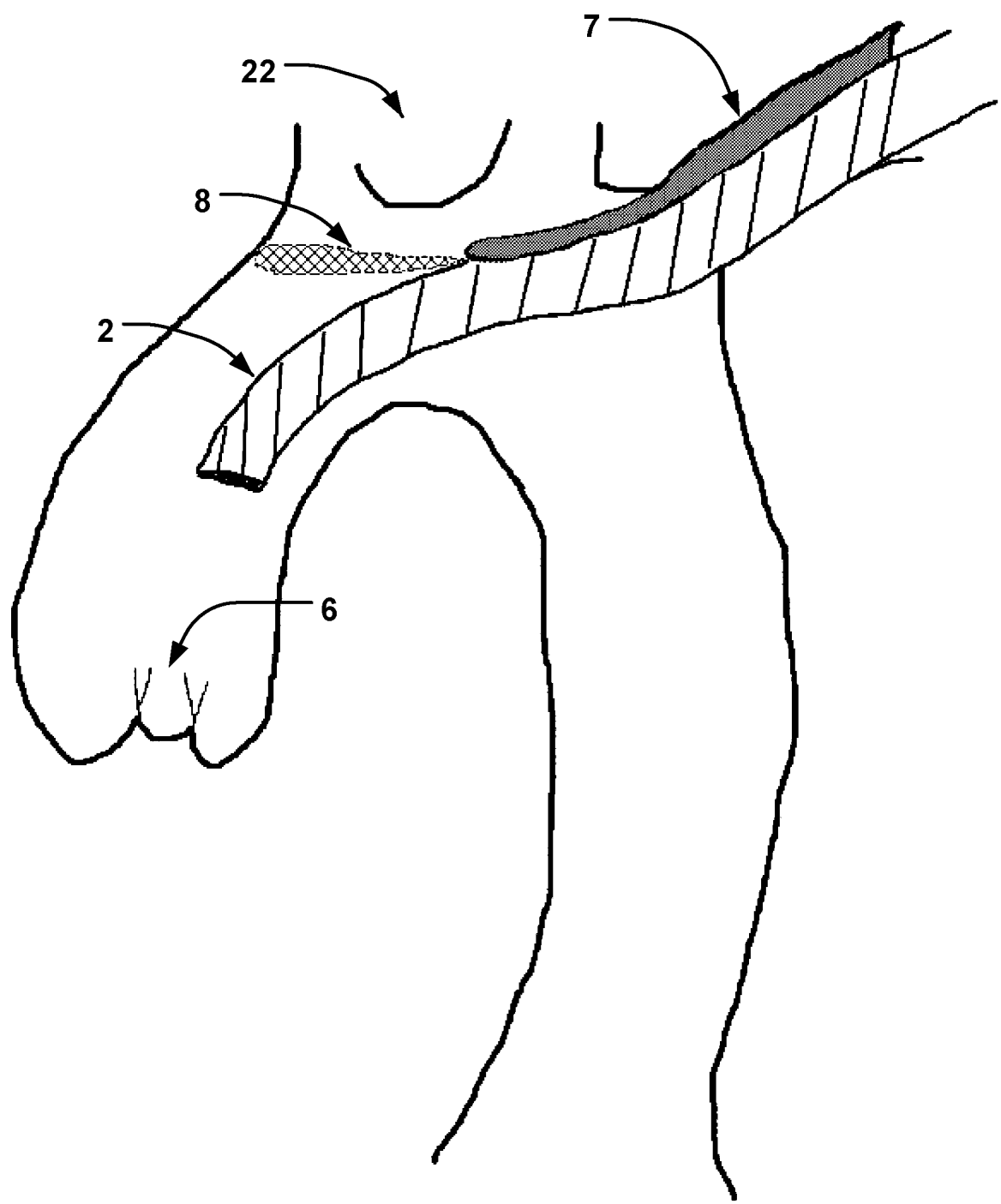
FIG. 4D is a schematic illustration of the elongate sheath delivered transaxillary to a cardiac valve, and the sheath is in the locked configuration arranged relative to an aortic cardiac valve, and the expandable units being withdrawn after positioning the sheath.
Figure 4E:
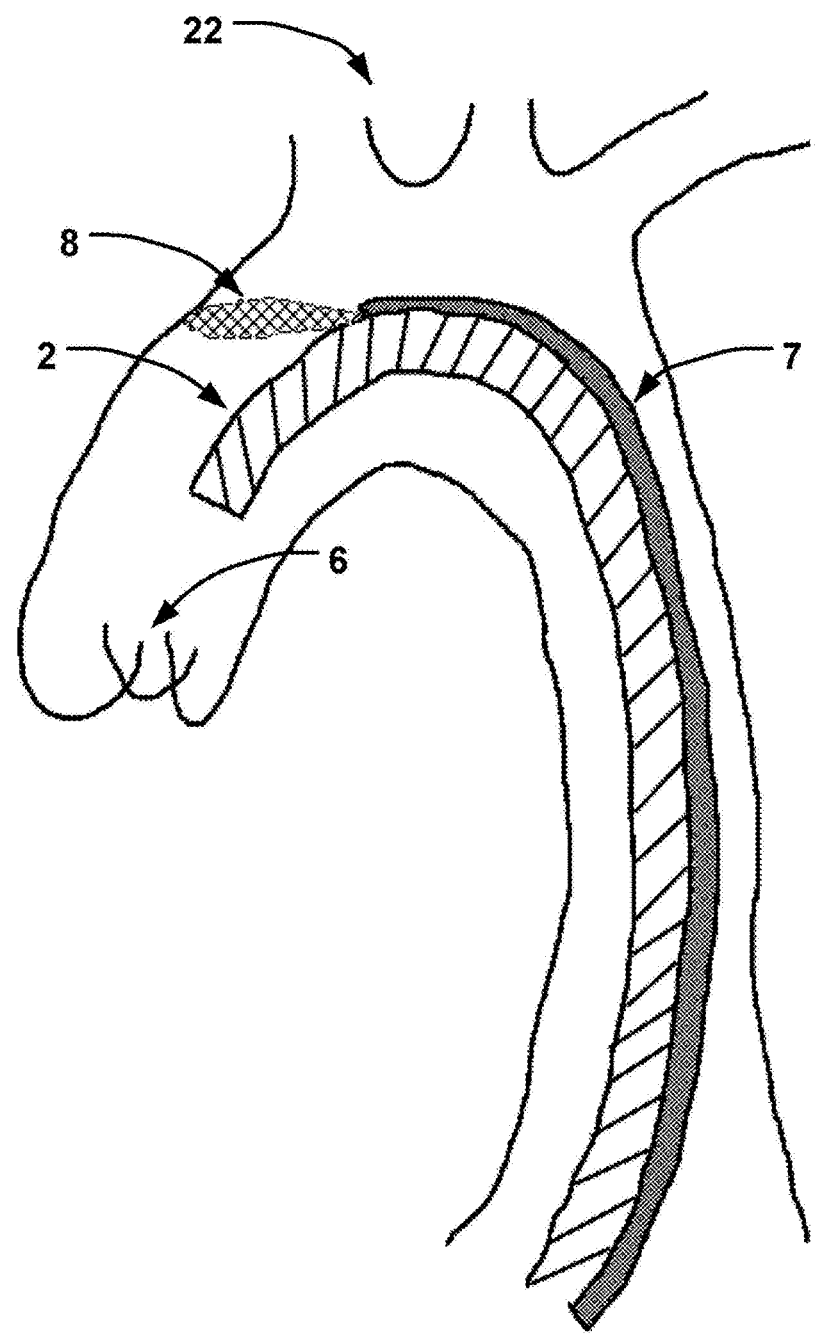
FIG. 4E is a schematic illustration of the elongate sheath delivered transfemorally to a cardiac valve, where an embolic protection filter is deployed and the sheath in the locked configuration.
Figure 4F:
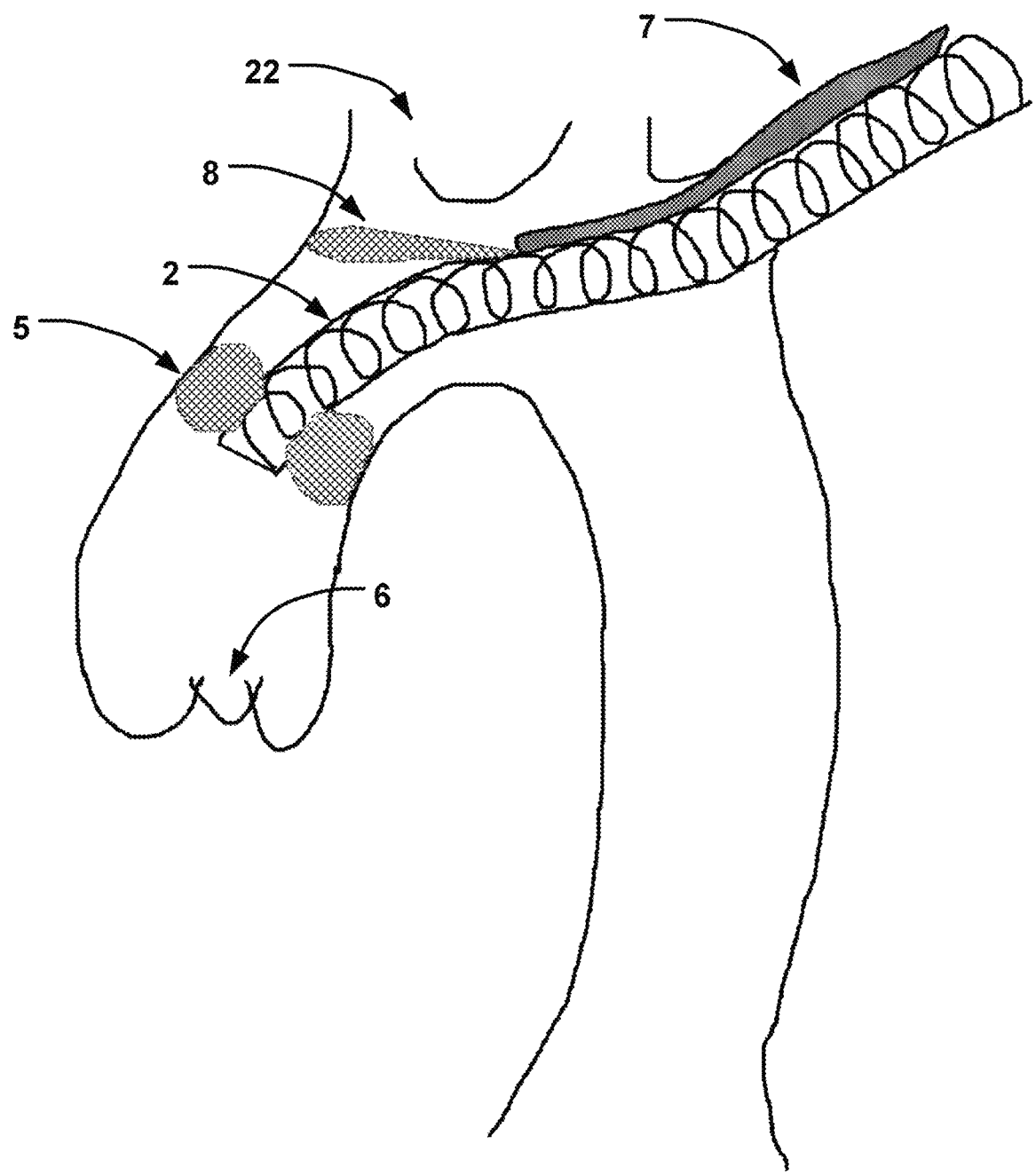
FIG. 4F is a schematic illustration of the elongate sheath delivered transaxillary to a cardiac valve, and where the relaxed sheath is positioned in relation to the cardiac valve by expandable units of the sheath.

The expandable unit may be integrally formed with the sheath, as seen in FIG. 4F.

Thus, the expandable units do not affect the cross section of the lumen of sheath 2. Upon returning to the unexpanded state, e.g. by deflating balloons of the expandable units 5, a delivery of a medical device through the catheter lumen may be made without the need to retract the expandable units 5.

The expandable units provide for a defined positioning of the distal en of the catheter sheath 2 in an anatomical structure, like a blood vessel, an atrium or cardiac chamber, relative a cardiac valve. This allows for a precision delivery of a medical device through the catheter device.

Movements of certain anatomical structures are very limited over the cardiac cycle. For instance the aortic arch is relatively stable and the locked catheter will stay substantially in the same spatial orientation, direction, and distance to the cardiac valve as during the final positioning provided by the expanded expandable units 5.

The catheter may thus be positioned relative a cardiac valve in an anatomical structure.

The catheter may be locked in the locked configuration along its entire length by having sets of expandable anchoring units at a longitudinal distance from each other, see example in the figures.

A distal portion may for instance be the portion arranged in the ascending aorta, the aortic arch and the descending aorta, as shown in FIG. 4E.

FIG. 4D is a schematic illustration of the elongate sheath delivered transaxillary to a cardiac valve, here the aortic valve 6, and relative to an aortic cardiac valve 6.

FIG. 4E is a schematic illustration of the elongate sheath delivered transfemorally to a cardiac valve.

In FIGS. 4D and 4E, the expandable units 5 are not shown, as they are either retracted from the sheath, or returned to their low profile unexpanded/collapsed configuration in the sheath.

Figure 4G:
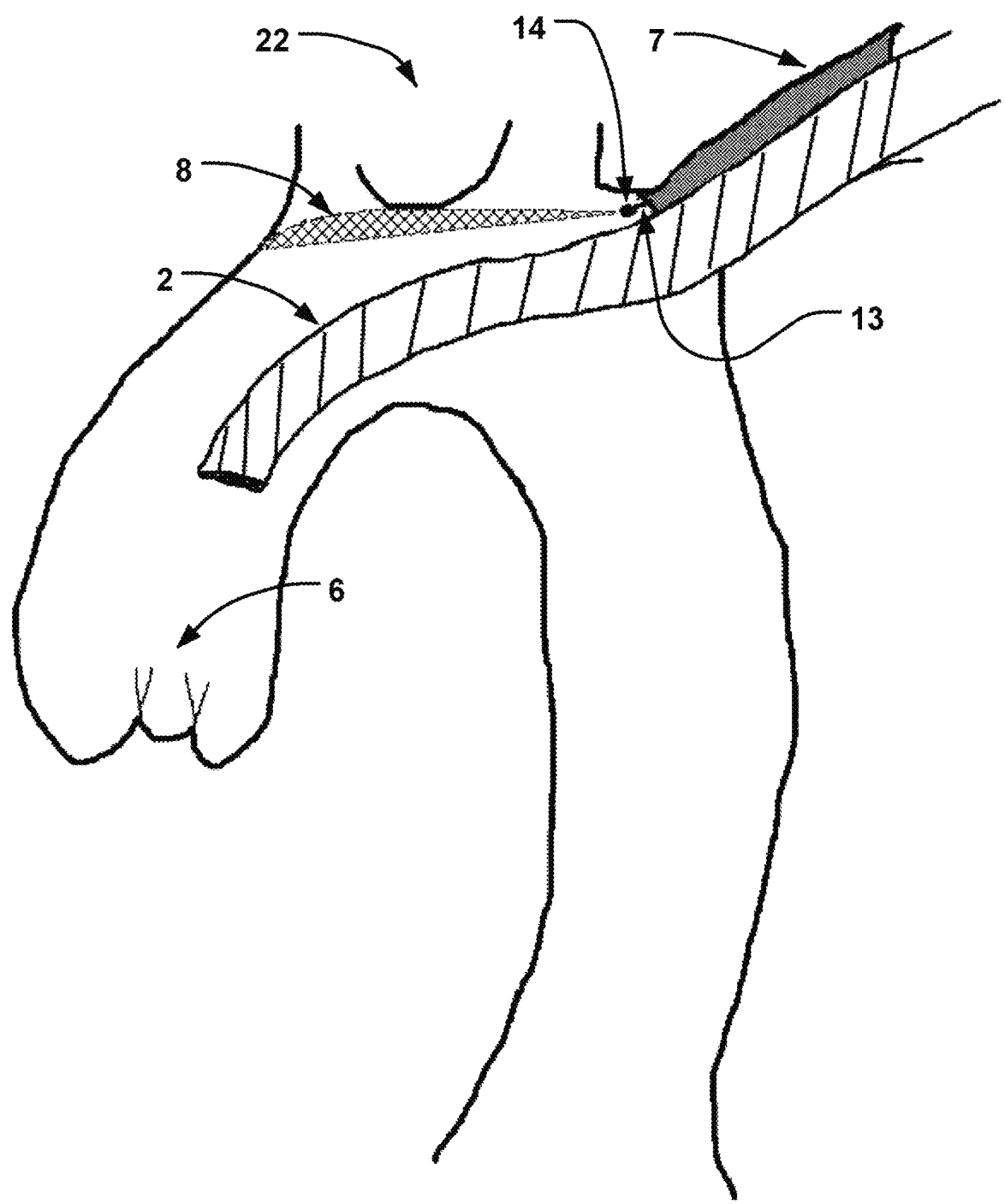
FIG. 4G is a schematic illustration of the elongate sheath delivered transaxillary to a cardiac valve, and where an embolic protection filter is deployed over the vessels in the aortic arch via a second channel of the sheath.
Figure 4H:
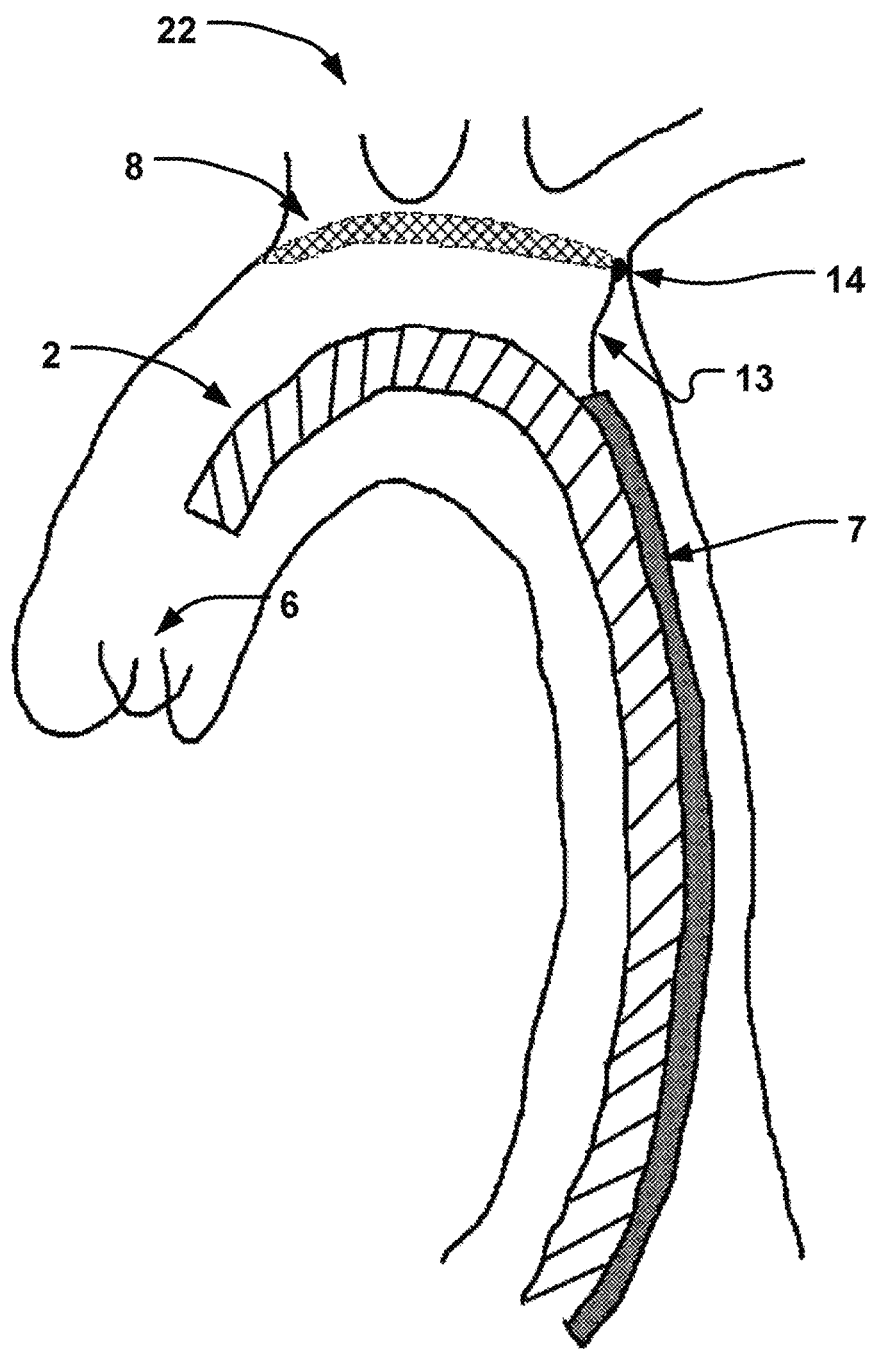
FIG. 4H is a schematic illustration of the elongate sheath delivered transfemorally to a cardiac valve, and where an embolic protection filter is deployed over the vessels in the aortic arch via a second channel of the sheath.

In FIG. 4G-H the sheath of the device passes alongside branch vessels in the aortic arch.

In embodiments, such as illustrated in FIG. 4A-H a catheter 1 having a second channel 7 that extends parallel on the outer portion or the inner portion of the elongate sheath 2 is depicted. This channel 7 allows for the delivery of further units or liquids to aid the procedure to place the medical device, when the lumen of the elongate sheath 2 is used for the elongate member 4 or medical device.

The second channel 7 may be an integral part on the inside or outside of the elongate sheath 2. This has the advantage of being relatively cheap to manufacture by an extrusion method.

In FIGS. 4A-H, a sheath device is depicted. Interaction with the side walls in the aortic arch is therefore also kept at the minimum, avoiding scraping off further debris to be transported with the blood stream. Simultaneously, the aortic arch is kept open for unrestricted navigation of the sheath 2.

By having a second channel in the sheath 2, the distal end of the sheath can be positioned appropriately at the valve, by the stabilizing and anchoring effect of the protection unit 8 extending from the second channel, while medical device can be delivered through the lumen of the sheath without any hindrance from the protection unit 8 or e.g. expandable units such as balloons.

Blood flow is kept open efficiently by such a compact device.

Figure 2A:
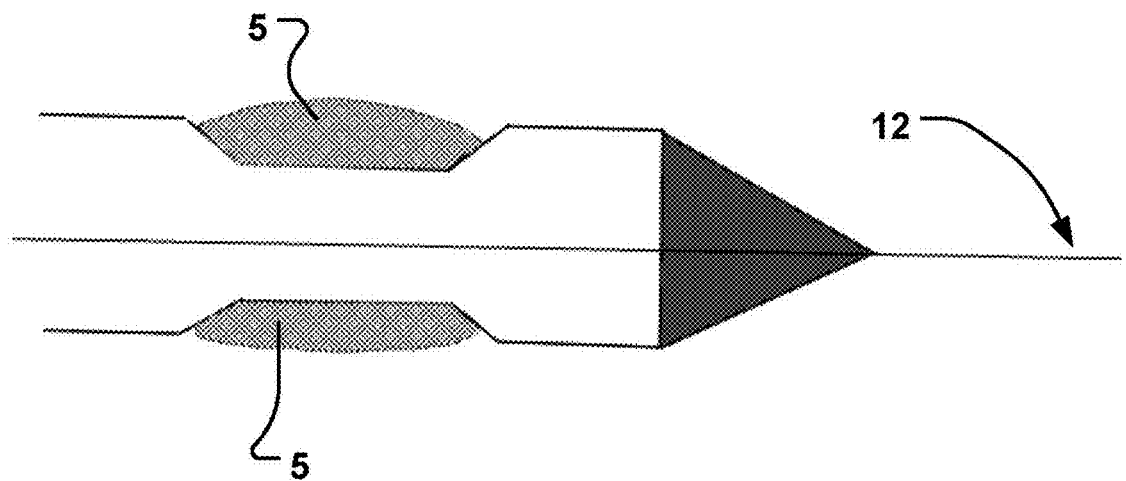
FIG. 2A is a schematic illustration of the distal end portion of the elongate member with the radially expandable units in the collapsed configuration.
Figure 2B:
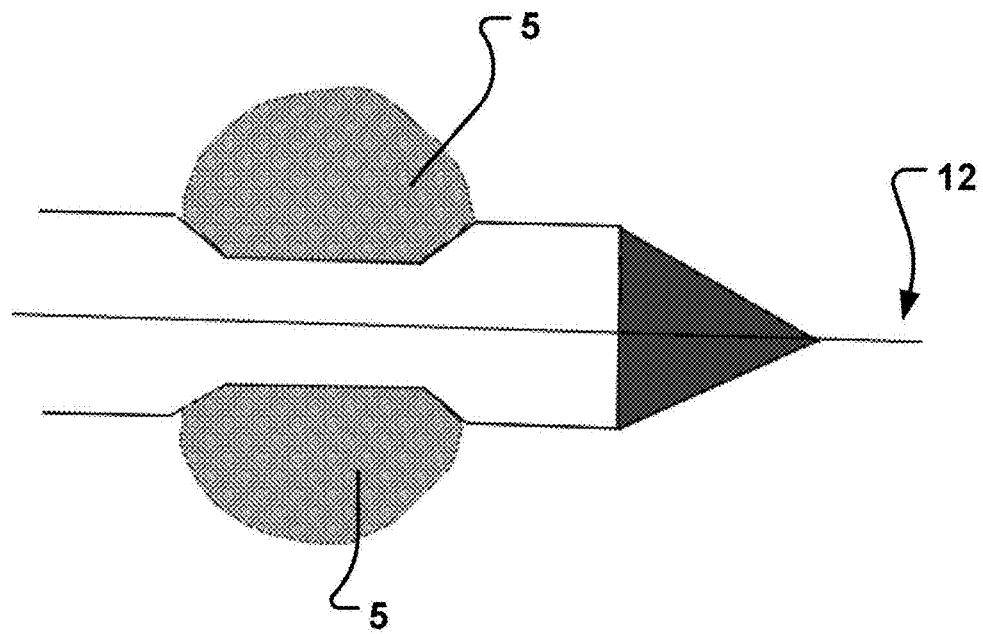
FIG. 2B is a schematic illustration of the distal end portion of the elongate member with the radially expandable units in the expanded configuration.
Figure 2C:
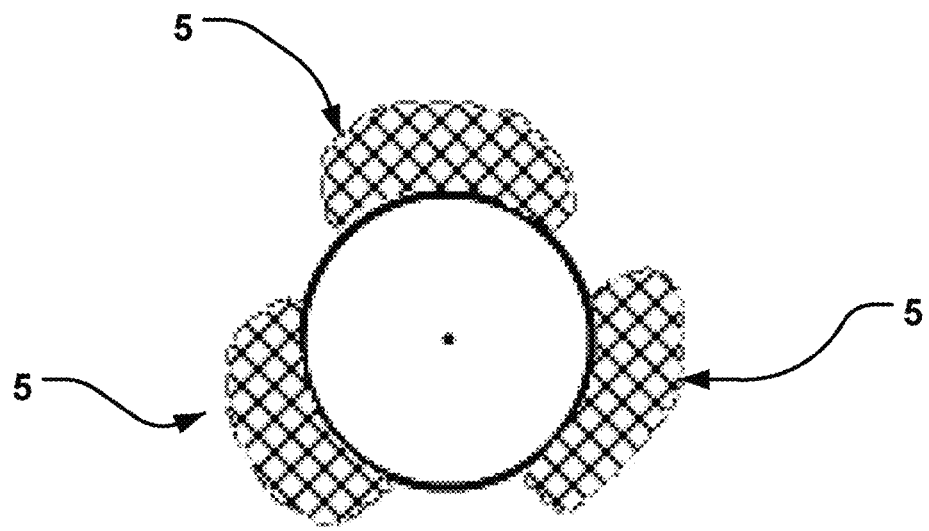
FIG. 2C is a schematic illustration frontal view of the distal end portion of the elongate member with the radially expandable units in the collapsed configuration.
Figure 2D:
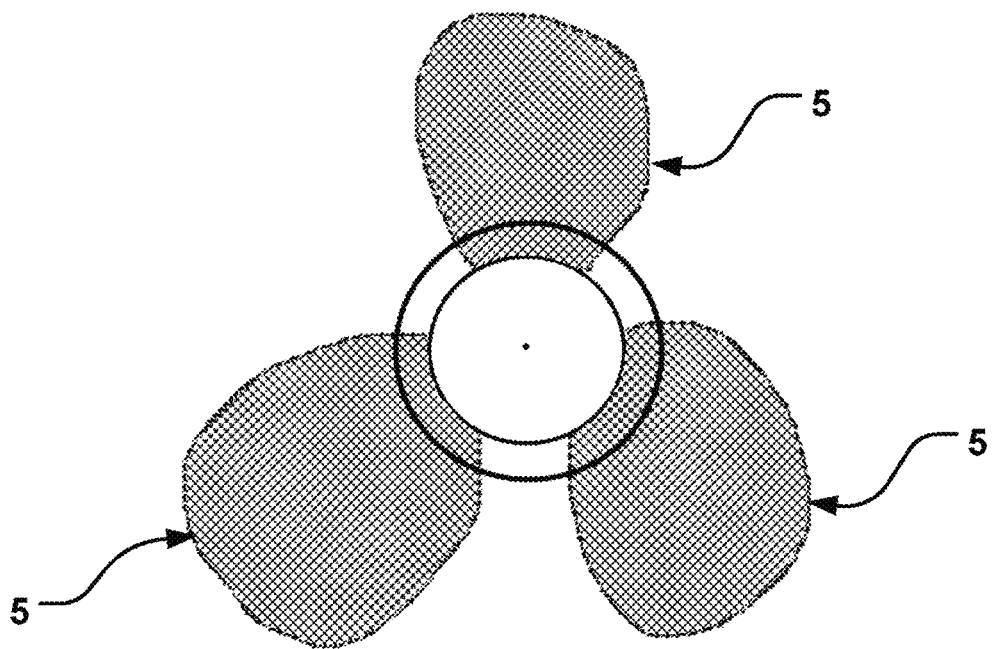
FIG. 2D is a schematic illustration frontal view of the distal end portion of the elongate member with the radially expandable units in the expanded configuration.
Figure 3A:
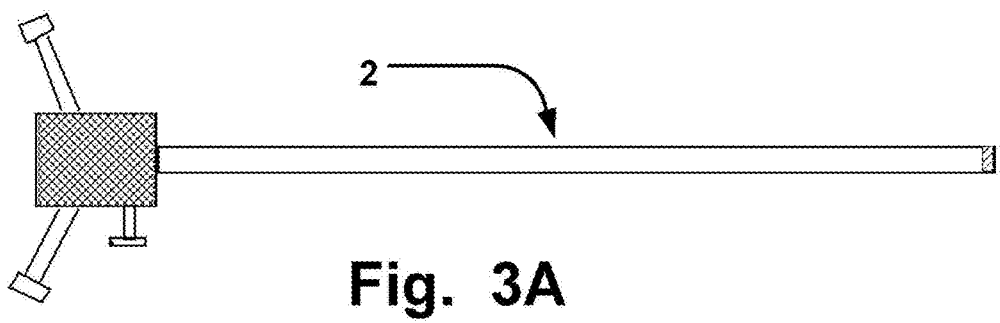
FIG. 3A, 3B, 3C, 3D are schematic illustrations of embodiments of the elongate sheath in the flexible, unlocked configuration.
Figure 3B:
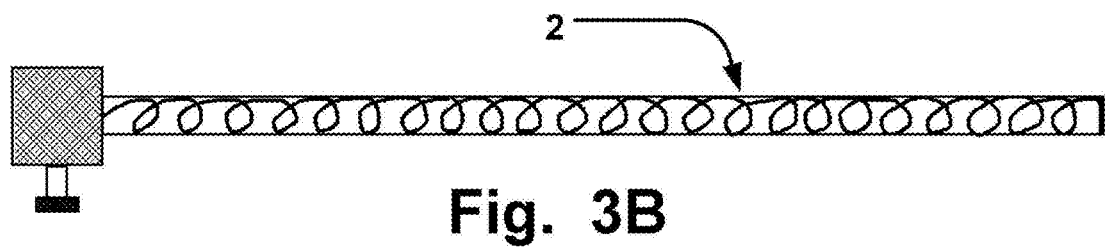
Figure 3C:
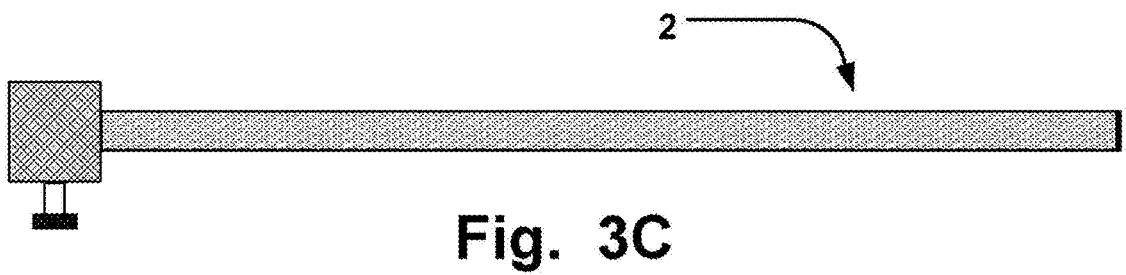
Figure 3D:
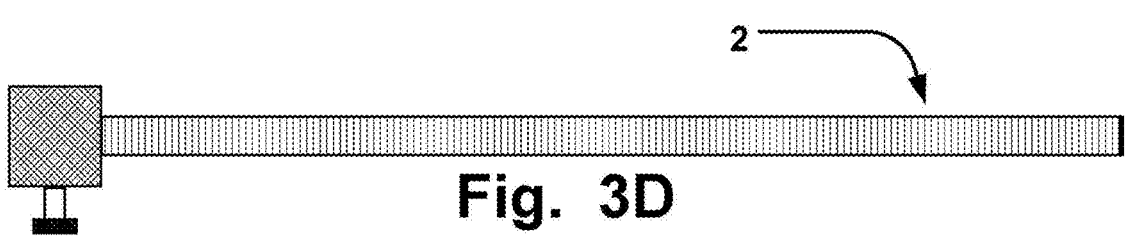
Figures 3E, 3F, 3G:
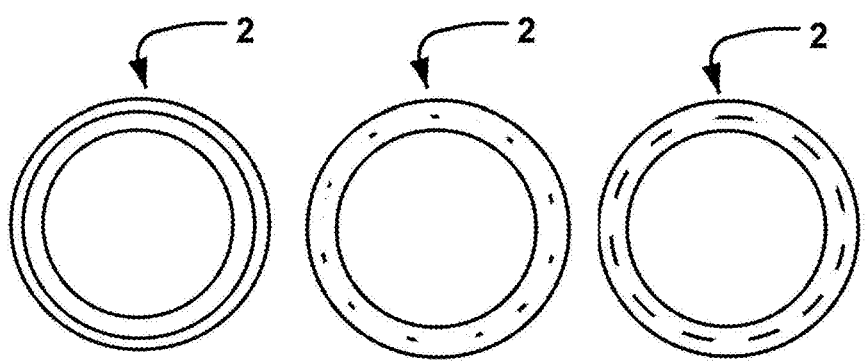
FIG. 3E is a schematic illustration of the cross sectional view of the elongate sheath in the unlocked state.
FIG. 3F is a schematic illustration of one embodiment of the cross sectional view of the elongate sheath in a locked state.
FIG. 3G is a schematic illustration of another embodiment of the cross sectional view of the elongate sheath in the locked state.

The elongate member 4 may be comprised of three balloons positioned radially equidistant around the longitudinal axis (See FIGS. 2C and D). Fewer or more balloons are possible, as well as alternative expansion units such as expandable mechanical levers, or swellable units for example retractable sponges. The expansion units 5 allow for optimal positioning of the elongate sheath 2 in relation to the aforementioned cardiac valve 6. The multiple balloon expansion unit can be expanded (See FIG. 2D) using a variety of means for example using a fluid means or where appropriate gaseous means. The balloons can also be individually or simultaneously expanded as well as inflated to differing pressures independently of the other expanding units.

Alternatively, the elongate member 4 is retractably inserted into the elongate sheaths 2 lumen to a length equal to the distance between the distal end 9 and the second proximal marker 10. In this embodiment proximal markers 10 and 11 are used to guide the positional orientation of the distal end portion 9 and thus provide for optimal alignment of the expandable units 5 with the portion of the elongate sheath 2 to be expanded. This facilitates safe positioning at the desired valve region.

In a further embodiment the elongate sheath 2 is comprised of radiopaque material, facilitating visualization of the elongate sheath 2 which provides for optimal positioning of the elongate sheath 2 for delivery of the medical device. Alternatively radiopaque fiducial markers on the elongate sheath 2 can be used for optimal positioning of the sheath 2 within the body of the patient.

The embodiment shown in FIGS. 2A and B, includes a guide wire 12 which is firstly positioned within the patient which facilitates optimal transit of the elongate sheath 2 and elongate member 4 to the desired anatomical site.

The locked elongate sheath 2 may be used in medical procedures to delivery of a medical device to the cardiac valve 6, which could include an artificial heart valve prosthesis, or similar devices.

Figure 5:
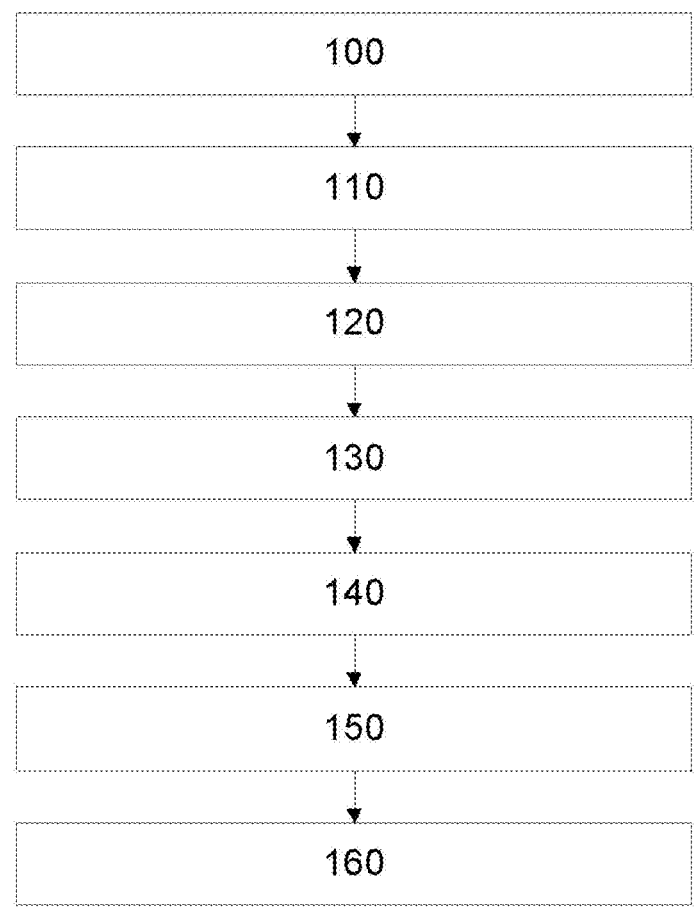
FIG. 5 is a flowchart for a method of implanting a medical device.

The elongate sheath 2 maybe a constituent of a medical system devised for transvascularly delivering a medical device to a cardiac valve 6 of a patient. The method as depicted in FIG. 5 initially comprises 100 minimally invasively either transfemorally (See FIG. 4E) or transaxillary (See FIG. 4D) introducing a catheter 1 comprising an elongate sheath 2 with a lumen in a relaxed state into the patients vascular system. Step 110 involves the distal end 3 of said elongate sheath 2 being navigated through the vascular system to the desired cardiac valve, FIG. 4A. The next step in the system 120, involves the elongate member 4 with a distal end portion 9 comprising a plurality of radially expandable units 5, being inserted into the lumen of the elongate sheath 2, whereupon it is advanced through the elongate sheath 2 to the distal end of the elongate sheath 2, FIG. 4B. Alternatively, expandable units 5 of the sheath may be expanded at this stage (without introducing an elongate member 4 into the sheath, FIG. 4F. Whereupon step 130 is initiated which involves the plurality of radially expandable units 5, being radially expanded to temporarily position in relation to the cardiac valve 6 the elongate sheath 2, (See FIGS. 4B and F).

After delivery of the medical device, or similar, the expandable units 5 of a sheath 2 are brought back to the non-expanded state.

A medical device can thus be delivered through the lumen of the anchored and precisely positioned elongate sheath 2 to the heart valve 6. This delivery is done with high spatial precision. Blood flow in the lumen around the anchored sheath 2 is maintained in-between the anchoring unit(s) or radially distally of some anchoring units when not in lumen wall apposition. Partially expanded anchoring units may contribute to mechanical stability of the sheath in the lumen, a pulsatile movements of the sheath may be dampened by intermittent apposition of the anchoring units to interior wall tissue of the lumen.

The medical device may for instance be a cardiac valve repair or replacement device.

When the medical device is delivered, release of the anchoring unit(s) to return the elongate sheath 2 to the released delivery state can now be performed (step 160) with the subsequent withdrawal of the elongate sheath 2 from the vasculature of the patient.

The embolic protection unit as shown in FIGS. 4A-H, may be retracted after the release of the anchoring unit(s).

To ensure the optimal positioning of the elongate member 4 when it is inserted into the elongate sheath 2, the elongate member 4 is inserted to a length which is equal to the distance between the distal end and the second proximal marker 10 of the elongate member 4. Primarily the elongate sheath 2 will be centrally positioned in relation to the cardiac valve 6, which facilitates optimal delivery of the medical device, although other positions off-center could also be desirable.

The medical system is primarily used for the delivery of a medical device to be affixed to the particular cardiac valve 6, which include the aortic and mitral valves of a patient. After delivery of the medical device to the cardiac valve 6, the medical device delivery system is withdrawn through the lumen of the elongate sheath 2.

The device provides for a 1:1 response for the operator thanks to long introducer channel No problems with twisted aorta anatomy No problems with plaque scraping No problems with delivering the stiffer type aortic stent valves to navigate around aortic arch with reduced stroke risk The sheath is soft preferably in an example flexible, at least the distal part. It is like a sloppy catheter in an example.

The sheath may have a pre-shaped bend optionally, it bends for instance when the introducer/dilator is withdrawn. It may bend to an arc formed shape, circular.

A stiffer dilator may be provided to stiffen the introducer during introductions from within This prevents the introducer sheath from kinking or collapsing, "simulates" a stiff (short) introducer. Then dilator withdrawal and push forward long soft introducer up to aorta descendens past side vessels and atop aortic valve is made.

A medical procedure is disclosed for positioning distal orifice of introduction catheter adjacent aortic valve.

Balloon expansion is preferably provided for target precision positioning of a distal orifice of the delivery device, preferably centering thereof A slotted Crown may be provided to produce partial/multiple balloon segments as shown in the figures. The "crown" may be positioned exterior to single lobe balloon to create multiple lobe balloons (anchoring units). Rigid webs that resist inflation pressure to create lobes expandable from interspaces between crowns webs. It is particularly well working with latex/rubber/elastic balloon(s) to create inflatable lobes. Inflatable lobes are adaptable to be in apposition with inner lumen wall of tubular body structures.

A single balloon with a single inflation channel may be divided into one or more lobes depending on the slots of the crown. The slots of the crown element may have a selected length and width to provide a desired lobe. The balloon material is elastic, such that the balloon can form expandable lobes upon inflation. The material of the balloon is elastic, such as for instance elastic rubber or latex. Balloon material, elasticity and thickness determine together with inflation pressure (preferably saline inflation liquid) the size and radial expansion of the lobe(s) to provide advantageous apposition, positioning and potentially securing of the catheter in the body lumen such as a vessel.

The crown is a tubular element than can be slid over the catheter to the position of a balloon. It can be made of sufficiently stiff material to resist inflation pressure at the one or more web(s) between the one or more slot(s) allowing expansion of balloon lobes.

As shown in the figures depicting the crown:

Thus, the system and catheter create a working channel to an aortic valve.

Alternative access may be made through artery, left arm, down to the aortic valve (not shown).

Some embodiments of the sheath include a thin condom type sheath having an open distal end orifice. The sheath of this example is preferably not stiff. It is preferably highly Flexible. It has preferably a low profile. It is thus atraumatic. It is preferably hydrophilic or coated with a hydrophilic agent. It is preferably elastic.

The sheath ends proximally of the distal end of the device sheath to be delivered, e.g. an artificial heart valve sheath over which the condom type sheath with at least one expansion element is positioned (coaxially). The sheath may be pre mounted, part of a delivery system The expandable members are expanded, e.g. when provided as balloons they are Inflated, when in position at the target site.

Several sets of expansion elements like one or more balloons along length of catheter/sheath may be provided advantageously. This provides better locking/securing to the vessel lumen at the position of expansion. This multiple sets of expansion elements prevents kinking of the delivery catheter when expandable members are expanded. They also in addition or alternatively prevent rotation of the delivery catheter in the vessel lumen when expandable members are expanded.

It is provided in an example a catheter device for transvascular delivery of a medical device to a target region, such as a heart valve region, of a patient. It comprises an elongate sheath with a lumen, a proximal end, a distal end, and a distal end portion including said distal end is configured to be positioning at, or in the vicinity to, or adjacent to said target region, such as said heart valve region. The elongate sheath preferably has an increasing flexibility towards said distal end. Increased flexibility may be provided by a thinner material of the catheter wall towards the distal end, e.g. at the distal end region.

The catheter device according to the example, has at least one, preferably a plurality of expandable units being arranged for temporarily positioning said elongate sheath in relation to said cardiac valve when in an expanded state.

The catheter device according to the example may additionally or alternatively have an elongate member with a distal end portion comprising the plurality of radially expandable units, wherein the elongate member is retractably insertable into the lumen.

The catheter device according to the examples may additionally or alternatively have the plurality of radially expandable units in the form of one or more expandable balloons, preferably three balloons positioned radially equidistant around a longitudinal axis of the elongate sheath. The interspace between the balloon(s) or lobes provides for continued flow of body fluid, like blood, urine, air, past the set of one or more balloons/lobes/expandable units to be expanded towards the lumen wall at a target site of the catheter.

The catheter device according to the examples may additionally or alternatively have the plurality of radially expandable units comprise alternatively or in addition expandable mechanical levers, or swellable units, such as sponges, collapsible and/or retractable into the sheath.

The catheter device according to the examples may additionally or alternatively have the medical device being an artificial replacement valve or a valve repair device, wherein the cardiac valve preferably is an aortic valve of the patient.

The catheter device according to the examples may be provided in a kit of the catheter device and a medical device for delivery to a cardiac valve region, such as an artificial replacement valve.

Alternatively, or in addition, a system is provided for transvascularly delivering a medical device to an aortic cardiac valve region of a patient. The system includes a catheter comprising an elongate catheter sheath with a lumen for minimally invasively introducing into the vascular system, the catheter being configured to transvascularly deliver an artificial heart valve to the aortic cardiac valve region.

The catheter sheath has a distal end configured to transvascularly navigate through the vascular system upstream the aorta to a position at and/or downstream the aortic cardiac valve.

A plurality of radially expandable units is provided at least temporarily proximate the distal end of the catheter sheath and at an exterior of the catheter sheath. At least one of the radially expandable units is configured to be in apposition with the interior vessel wall in the ascending aorta downstream the aortic valve and upstream all side branch vessels of the aortic arch.

The radially expandable units are arranged for expanding to temporarily position the distal end in relation to the cardiac valve.

The expandable units are arranged to allow for blood flow outside the sheath and past lobes of the radially expandable units when in a position for delivering the artificial aortic valve.

Alternatively, or in addition, a catheter device is provided for transvascular delivery of a medical device to a target region, such as a heart valve region, of a patient, comprising an elongate catheter sheath with a lumen, a proximal end, a distal end, and a distal end portion including the distal end is configured to be positioning at, or in the vicinity to, or adjacent to the target region, such as the heart valve region; and a cover sheath arranged coaxially outside of the elongate catheter sheath.

The catheter sheath has distal end configured to transvascularly navigate through the vascular system upstream the aorta to a position at and/or downstream the aortic cardiac valve.

The cover sheath includes at least one or a plurality of radially expandable units proximate the distal end of the catheter sheath and at an exterior of the catheter sheath. At least one of the radially expandable units is configured to be in apposition with the interior vessel wall in the ascending aorta downstream the aortic valve and upstream all side branch vessels of the aortic arch.

The radially expandable units are arranged for expanding to temporarily position the distal end in relation to the cardiac valve.

The expandable units are arranged to allow for blood flow outside the sheath and past lobes of the radially expandable units when in a position for delivering the artificial aortic valve.

The cover sheath ends proximal of the catheter sheath distal end.

The cover sheath has preferably a higher flexibility than the flexibility of the delivery catheter.

At least one of the radially expandable units is for instance configured to be in apposition with the interior vessel wall in the ascending aorta downstream the aortic valve and upstream all side branch vessels of the aortic arch.

The cover sheath has in an example an increasing flexibility towards the distal end. This allows for better navigation around the aortic arch. This also allows for a low profile catheter and improved deliverability of a medical device, such as an artificial heart valve through the sheath.

The cover sheath is for instance elastic. It may have a lesser inner lumen diameter than an outer diameter of the delivery catheter, wherein the sheath is arranged outside the delivery catheter by stretching over the delivery catheter's outside an along the delivery catheter outside.

The cover sheath has preferably a length shorter than a length of the delivery catheter.

The device of these examples may be combined with an introducer device configured to provide vascular, such as femoral access to the patients vascular system, wherein the introducer has a shorter length than the delivery catheter, and preferably a lower flexibility than the delivery catheter and the cover sheath. This allows for most advantageous delivery of a medical device over a long distance to a position remote of the puncturing site entering the vascular system (e.g. femoral approach).

The cover sheath includes in examples balloons/stabilizers and has a distal end with an orifice that ends proximally of the delivery catheter's distal end. The sheath may be arranged coaxially outside of delivery catheter (preferably with low profile/diameter increase of delivery catheter).

The cover sheath preferably has a distal end with an attachment unit to the delivery catheter at the distal end of the cover sheath. The attachment unit is preferably an adhesive unit, a force fit unit (e.g. distal end contracting onto delivery catheter), or a mechanical fixation unit (outside ring, clamp, lock ring, hook, barb, interference fit).

The device of any of the examples may include one or more slotted crown unit(s) having a plurality of slots for passage of a portion of an interior inflation balloon and configured to produce lobes of the balloon through the slots and radially outside the slots.

A plurality of crown units may provide a plurality of sets of expandable balloons along the length of the sheath on which the crowns are attached.

Additionally or alternatively, the sheath and/or catheter may have a lubricious inside, such as of Teflon or Teflon coating.

Additionally or alternatively, the sheath and/or catheter having a reinforcement braiding to avoid kinking.

The multiple sets of the anchoring units (expandable units) may be provided at a longitudinal distance from each other at the sheath. Sets may be configured to be arranged a) in the ascendens aorta and b) in the descendens aorta besides other positions.

This may provide for improved hemodynamic stability during positioning in the aortic arch. Each set of anchoring units allows for blood flow in-between the anchoring units along the sheath exterior. Hemodynamic pressure waves may be smoothed out and improve hemodynamic stability having several sets of anchoring units arranged in that manner, see Figures.

A method of transvascularly delivering a medical device to a cardiac valve of a patient is provided. The method comprises at least the steps of: introducing a catheter comprising an elongate sheath with a lumen in a relaxed state into the vascular system; navigating a distal end of the elongate sheath through the vascular system to the cardiac valve; expanding an embolic protection unit from a second channel in the sheath to cover ostia of the side branch vessels in the aortic arch and to stabilize a distal end of the sheath at the cardiac valve, and delivering a medical device through the lumen of the locked elongate sheath to the heart valve while the embolic protection unit covers the ostia.

The method may include radially expanding expandable units of the catheter or an elongate member positioned beyond a distal end of the sheath, to temporarily position in relation to the valve the elongate sheath; and optionally delivering a medical device through the lumen of the elongate sheath to the heart valve, wherein the elongate sheath is preferably locked in position in the lumen by expandable member(s).

The method may additionally include inserting an elongate member with a distal end portion comprising a plurality of the radially expandable units, into the lumen of the elongate sheath; advancing the elongate member through the elongate sheath to the distal end of the elongate sheath; retracting the expandable units and withdrawing the elongate member from the lumen of the elongate sheath.

The present invention has been described above with reference to specific embodiments. However, other embodiments than the above described are equally possible within the scope of the invention. Different method steps than those described above, may be provided within the scope of the invention. The different features and steps of the invention may be combined in other combinations than those described. The catheter may be positioned and locked in other cardiac anatomical structures than illustrated. Medical devices delivered through the catheter sheath may be any medical device to be delivered to the cardiac valve tissue. The scope of the invention is only limited by the appended patent claims.

The invention claimed is:

1. A catheter device for transvascular delivery of a medical device including an artificial heart valve prosthesis to a target aortic heart valve region of a patient including an aortic cardiac valve; said device comprising
    an elongate catheter sheath with a lumen for receiving a medical device delivery system for said artificial heart valve prosthesis, a proximal end, a distal end, and a distal end portion including said distal end for being positioned at said target aortic heart valve region and downstream said aortic cardiac valve, and
    a cover sheath mounted coaxially on the outside of said elongate catheter sheath;
    said elongate catheter sheath having said distal end and being transvascularly navigateable through said vascular system upstream the patient's aorta to a position in said aorta downstream said aortic cardiac valve;
    wherein said cover sheath ends proximal of said catheter sheath's distal end; said cover sheath including at least one radially expandable unit arranged proximate said distal end of said catheter sheath and at an exterior of said catheter sheath when coaxially arranged; wherein at least one of said at least one radially expandable unit is configured to be in apposition with the interior vessel wall in the ascending aorta downstream said aortic valve and upstream all side branch vessels of said aortic arch;
    wherein said at least one radially expandable unit is arranged for expanding to temporarily position said distal end of said elongate catheter sheath in relation to said cardiac valve;
    whereby said at least one radially expandable unit is arranged to allow for blood flow outside said cover sheath and past at least one lobe of said at least one radially expandable unit when said elongate catheter sheath is in a position for delivering said artificial heart valve prosthesis.

2. The device of claim 1, wherein said cover sheath is pre-bent at a distal portion and has preferably a pre-shaped arc-formed bend shape.

3. The device of claim 1, wherein said cover sheath comprising multiple sets of said at least one expandable unit at a longitudinal distance from each other at said sheath.

4. The device of claim 3, wherein a first set is positioned at said cover sheath arrangeable in the ascendens aorta and a second set arrangeable in the descendens aorta.

5. The device of claim 1, wherein said cover sheath has a higher flexibility than said elongate catheter sheath.

6. The device of claim 1, wherein said cover sheath has an increasing flexibility towards said distal end of said cover sheath.

7. The device of claim 1, wherein said cover sheath is elastic and has a lesser inner lumen diameter than an outer diameter of said elongate catheter sheath, wherein said cover sheath is arranged outside said delivery catheter by stretching over said elongate catheter sheath's outside and along said elongate catheter sheath outside.

8. The device of claim 1, wherein said cover sheath has a length shorter than a length of said elongate catheter sheath.

9. The device of claim 1, in combination with an introducer device configured to provide vascular, such as femoral access to said patients vascular system, said introducer having a shorter length than said elongate catheter sheath, and a lower flexibility than said elongate catheter sheath and said cover sheath.

10. The device of claim 1, wherein said cover sheath's distal end has an orifice that ends proximally of the elongate catheter sheath's distal end.

11. The device of claim 1, said cover sheath having a distal end with an attachment unit for attachment to the elongate catheter sheath at the distal end of said cover sheath.

12. The device of claim 11, wherein said attachment unit is an adhesive unit, a force fit unit, such as said distal end contracting onto said elongate catheter sheath, or a mechanical fixation unit, such as an outside ring, clamp, lock ring, hook, barb, or interference fit.

13. The device of claim 1 including a slotted crown unit having a plurality of slots for passage of a portion of an interior inflation balloon and configured to produce lobes of said balloon through said slots and radially outside said slots.

14. The device of claim 1 said elongate catheter sheath having a lubricious inside, such as of PTFE, Teflon or Teflon coating.

15. The device of any of claim 1, said elongate catheter sheath having a reinforcement braiding to avoid kinking.

16. The catheter device of claim 1, wherein said at least one radially expandable unit comprises at least one expandable balloon, preferably three balloons positioned radially equidistant around a longitudinal axis of said elongate sheath.

17. The catheter device of claim 16, wherein said at least one radially expandable unit comprises expandable mechanical levers, or swellable units, such as sponges, retractable into said cover sheath.

* * * * *